(12) United States Patent
Klimenko et al.

(10) Patent No.: US 10,987,189 B2
(45) Date of Patent: Apr. 27, 2021

(54) MOVEABLE MRI MOVING APPARATUS

(71) Applicant: Sino Canada Health Engineering Research Institute (Hefei) Ltd., Hefei (CN)

(72) Inventors: Gordon A. Klimenko, Winnipeg (CA); Darrell Van Mol, East St. Paul (CA); John Saunders, Winnipeg (CA); Gong Zhang, Winnipeg (CA)

(73) Assignee: Sino Canada Health Engineering Research Institute (Hefei) Ltd., Hefei (CN)

( * ) Notice: Subject to any disclaimer, the term of this patent is extended or adjusted under 35 U.S.C. 154(b) by 0 days.

(21) Appl. No.: 16/747,150

(22) Filed: Jan. 20, 2020

(65) Prior Publication Data

US 2020/0249290 A1    Aug. 6, 2020

Related U.S. Application Data

(60) Provisional application No. 62/799,498, filed on Jan. 31, 2019, provisional application No. 62/799,510, filed on Jan. 31, 2019.

(51) Int. Cl.
*A61B 90/00* (2016.01)
*G01R 33/38* (2006.01)
(Continued)

(52) U.S. Cl.
CPC ............ *A61B 90/36* (2016.02); *A61B 5/0042* (2013.01); *A61B 5/0046* (2013.01); *A61B 5/055* (2013.01); *A61B 5/062* (2013.01); *A61B 34/20* (2016.02); *A61B 34/37* (2016.02); *A61B 90/11* (2016.02); *A61B 90/14* (2016.02); *A61B 90/37* (2016.02);
(Continued)

(58) Field of Classification Search
CPC ....... A61B 90/36; A61B 90/37; A61B 5/0046; G01R 33/283; G01R 33/307; G01R 33/34007
See application file for complete search history.

(56) References Cited

U.S. PATENT DOCUMENTS 4,875,485 A * 10/1989 Matsutani .............. G01R 33/28
600/415
8,295,905 B2 * 10/2012 Graves ................... G01R 33/28
600/411
(Continued)

*Primary Examiner* — G. M. A Hyder
(74) *Attorney, Agent, or Firm* — Adrian D. Battison; Ade & Company Inc.; Michael R. Williams

(57) ABSTRACT

Apparatus for imaging during surgical procedures includes an operating room for the surgical procedure and an MRI for obtaining images periodically through the surgical procedure by moving the magnet up to the table. The magnet wire is formed of a superconducting material such as magnesium di-boride or Niobium-Titanium which is cooled by a vacuum cryocooling system to superconductivity without use of liquid helium. The magnet weighs less than 1 to 2 tonne and has a floor area in the range 15 to 35 sq feet so that it can be carried on the floor by a support system having an air cushion covering the base area of the magnet having side skirts so as to spread the weight over the entire base area. The magnet remains in the room during surgery and is powered off to turn off the magnetic field when in the second position remote from the table.

23 Claims, 18 Drawing Sheets

(51) Int. Cl.

| | | |
|---|---|---|
| *G01R 33/385* | (2006.01) | |
| *A61B 5/055* | (2006.01) | |
| *G01R 33/3815* | (2006.01) | |
| *A61B 5/00* | (2006.01) | |
| *G01R 33/28* | (2006.01) | |
| *G01R 33/30* | (2006.01) | |
| *G01R 33/34* | (2006.01) | |
| *A61B 34/20* | (2016.01) | |
| *A61B 34/37* | (2016.01) | |
| *A61B 5/06* | (2006.01) | |
| *G01R 33/24* | (2006.01) | |
| *A61B 90/11* | (2016.01) | |
| *A61B 90/14* | (2016.01) | |
| *A61N 1/05* | (2006.01) | |
| *G01R 33/36* | (2006.01) | |

(52) U.S. Cl.
CPC ......... *A61N 1/0534* (2013.01); *G01R 33/246* (2013.01); *G01R 33/283* (2013.01); *G01R 33/307* (2013.01); *G01R 33/34007* (2013.01); *G01R 33/34084* (2013.01); *G01R 33/3614* (2013.01); *G01R 33/3802* (2013.01); *G01R 33/3804* (2013.01); *G01R 33/3815* (2013.01); *G01R 33/3856* (2013.01); *A61B 2090/374* (2016.02); *A61B 2503/04* (2013.01); *A61B 2505/05* (2013.01); *A61B 2560/0437* (2013.01); *A61B 2560/0443* (2013.01); *A61B 2562/164* (2013.01); *A61B 2562/182* (2013.01); *G01R 33/3403* (2013.01)

(56) References Cited

U.S. PATENT DOCUMENTS

| | | | |
|---|---|---|---|
| 9,138,145 B2* | 9/2015 | Klimenko | A61B 5/055 |
| 9,301,707 B2* | 4/2016 | Dahan | A61B 5/6889 |
| 9,575,148 B2* | 2/2017 | Winter | G01R 33/3802 |
| 2013/0235969 A1* | 9/2013 | Winter | A61B 6/5247 |
| | | | 378/4 |
| 2014/0152302 A1* | 6/2014 | Rapoport | G01R 33/3808 |
| | | | 324/307 |
| 2018/0224512 A1* | 8/2018 | Poole | G01R 33/5659 |
| 2020/0246095 A1* | 8/2020 | Zhang | A61B 34/20 |
| 2020/0246106 A1* | 8/2020 | Zhang | G01R 33/445 |
| 2020/0249289 A1* | 8/2020 | Zhang | G01R 33/246 |
| 2020/0249290 A1* | 8/2020 | Klimenko | A61B 90/36 |
| 2020/0249293 A1* | 8/2020 | Saunders | G01R 33/3614 |

* cited by examiner

MOVEABLE MRI MOVING APPARATUS

This application claims the benefit under 35 USC 119 (e) of Provisional applications 62/799,498 and 62/799,510 both filed Jan. 31, 2019.

This invention relates to a movable MRI system for use in surgical procedures.

BACKGROUND OF THE INVENTION

Magnetic resonance imaging (MRI) is a non-invasive imaging modality capable of distinguishing a wide variety of objects based on their intrinsic composition and also is an imaging technique that is capable of providing one-, two- or three-dimensional imaging of the object. A conventional MRI system typically includes a main or primary magnet that provides the main static magnetic field, B0, magnetic field gradient coils and radio frequency (RF) coils, which are used for spatial encoding, exciting and detecting the nuclei for imaging. Typically, the main magnet is designed to provide a homogeneous magnetic field in an internal region within the main magnet, for example, in the air space of a large central bore of a solenoid or in the air gap between the magnetic pole plates of a C-type magnet. The patient or object to be imaged is positioned in the homogeneous field region located in such air space. The gradient field used to convert distance into frequency and the RF coils used to transmit and receive signals from the patient are typically located external to the patient or object to be imaged and inside the geometry of the main or primary magnet(s) surrounding the air space.

Typically the uniform magnetic field B0 generated by the main magnet on the high field MRI systems (>1.0 Tesla) is generated and then remains on for the life of the magnet, although the field maybe boosted every now and then during the magnet's operating life. In conventional MRI devices, the patient is bought to the magnet, placed on a patient couch and then slid into the magnet with the region to be imaged placed as close to the isocenter of the magnet. This requires that the patient be either ambulatory or can be brought to the magnet on a gurney and slid into the magnet. There are many times when the physician would prefer to bring the MRI magnet to the patient since the patient is in a position where he/she should not be moved. Examples include patient undergoing surgical or interventional procedures where the physician needs an image or for patients such as stroke or accident victims who by their condition should not be moved.

Modern neurosurgery encompasses the surgical treatment of many complex conditions such as primary intracranial or spinal neoplasms, lesions of the cranium and cranial base, cerebral vascular disorders including arteriovenus malformations, cavernous angiomas and intracranial aneurysms, and inflammatory conditions. Concurrent with these changes, imaging by computerized tomography, magnetic resonance, positron emission tomography, and magnet wave processing provide greatly improved comprehension of brain structure and functional events. Imaging data have been incorporated into stereotactic space by a number of devices to allow a precise point access and volume comprehension for planning and trans-cerebral navigation, all with striking reduction in operative working corridor size. However, this imaging technology needs to be taken to the operating theatre so that changes that result from brain shift and tissue removal and the extent of surgical procedure can be accommodated. A number of surgical intraoperative MRI devices have been developed with the most popular being that sold by IMRIS. The challenge with this IMRIS device is that the installation requires extensive renovations to the hospital operating theatre which is very expensive and results in the operating theatre being unavailable for a significant period of time.

SUMMARY OF THE INVENTION

According to one aspect of the invention which can be used independently of other features set out herein there is provided an apparatus for use in surgical procedures comprising:

an operating room having a floor and walls containing an operating table for receiving a patient for a surgical procedure;

and a magnetic resonance imaging system for obtaining images of a part of the patient at a series of times through the surgical procedure for analysis by the surgical team to allow the surgical team to monitor the progress of the surgery, the magnetic resonance imaging system comprising:

a magnet system comprising a cylindrical magnet of magnet wire defining a cylindrical bore within which a part of the patient is located for placement within high magnetic fields generated by the magnet;

a control system for controlling and varying the magnetic fields;

a radio frequency transmission and detection system for eliciting and detecting from the part of the patient nuclear magnetic resonance signals, in response to the magnetic field, including an RF probe arranged to be located adjacent to the part of the patient;

and a computer and display monitor for decoding and displaying the detected signals;

a table support system mounting the magnet for movement relative to the table in a direction away from the first end of the table from a first position at the table to a second position remote from the table;

the first position of the magnet being arranged such that the part of the patient is positioned in the magnetic field of the magnet while the patient remains in place on the table;

the second position of the magnet being arranged such that the magnet is spaced from the first end of the table by a distance sufficient to allow the surgical team to move around the first end of table and to each side of the table to access the patient and sufficient to allow to allow the surgical team to carry out the surgical procedure;

wherein the magnet wire is formed of a superconducting material which is cooled by a cooling system to superconductivity without use of liquid helium.

Preferably the magnet wire is formed from magnesium di-boride which requires a temperature of around 40 degrees absolute which can be reached without use of liquid helium and typically using a vacuum cryo-cooling system having a vacuum pump. Other materials which can be used are Niobium Titanium and, possibly although less suitably, Niobium-Tin.

For example, using these techniques, the magnet can have a weight of less than 2 tonne and a floor area in the range 15 to 40 sq feet and typically around 35 sq feet which can be tolerated by most standard floor systems.

This allows preferably the magnet to be carried on a support system supported from the floor. In particular the support system can comprise an air cushion covering the base area of the magnet having side skirts so as to spread the weight over the entire base area. In order to be used in an operating theater, preferably the air cushion system is arranged so that it expels no particles from the side skirts.

While the magnet preferably floats on the air cushion to spread the load, preferably the support system is guided from the first position to the second position on guide rails.

In another preferred arrangement, the magnet is carried on a pair of side tracks in the manner of a skid steer loader so that the side tracks along the sides of the magnet base carry the weight and can be controlled sufficiently accurately to drive the magnet forward into position relative to the table. It will be appreciated that the magnet bore just fits along the table so that the accuracy of drive must be very high to ensure the required proper location of the magnet without the use of guide rails.

As explained in more detail hereinafter, also the tracks allow the magnet to be rotated about a vertical axis at or adjacent a center of the magnet so as to move a forward end of the magnet into a room in the required orientation.

An arrangement of this type can preferably allow the magnet to be powered off to turn off the magnetic field when in the second position. In this way the magnet can sit dormant in the same room as the operating procedure but preferably with the cooling system remaining on when the magnetic field is powered off. In this arrangement preferably the magnet dedicated solely to surgery within the operating room and remains in the room. Even though cost can be shared by multi-uses of the magnet, in this arrangement, the small construction of the magnet allowing it to be supported from the floor and the simple connection of the magnet to the cooling water and electrical supply allows it to be stalled in a very cost-effective manner. At the same time the magnet selected can provide more than 1 tesla which is sufficient to provide effective imaging.

To keep the weight down, the magnet has preferably a minimum bore diameter of the order of 60 to 70 cms, typically around 65 cms, and a length in the range 5 feet.

Again to maintain the overall dimensions as small as possible, in some cases the RF probe comprises local transceiver RF coils so as to avoid use of a cylindrical body coil at the bore which would otherwise increase the diameter of the magnet. However in other cases a body coil can be used within the bore particularly as a transmit coil with the receive coil being provided as a separate component particularly around the head.

In order to avoid shielding the whole room as it typically required from stray RF signals, preferably there is provided a shielding structure for excluding RF fields from the RF probe which comprises an arched support frame for extending over the patient and supporting a shielding fabric or screen material extending from the feet up to the location on the body which enters the bore, a metal sheet as part of the table located underneath the patient and extending across the table to the sides of the shielding fabric, a cylindrical shielding layer inside the bore and a hinged door on an end of the bore opposite the table and containing a shielding layer. The shielding material can be a screen material encapsulated in a plastics material so as to form a stiff structure which retains its shape as an arch when deployed over the patient on the table.

According to one aspect of the invention which can be used independently of other features set out herein there is provided an apparatus for use in surgical procedures comprising:

an operating room having a floor and walls containing an operating table for receiving a patient for a surgical procedure;

and a magnetic resonance imaging system for obtaining images of a part of the patient at a series of times through the surgical procedure for analysis by the surgical team to allow the surgical team to monitor the progress of the surgery, the magnetic resonance imaging system comprising:

a magnet system comprising a cylindrical magnet of magnet wire defining a cylindrical bore within which a part of the patient is located for placement within high magnetic fields generated by the magnet;

a control system for controlling and varying the magnetic fields;

a radio frequency transmission and detection system for eliciting and detecting from the part of the patient nuclear magnetic resonance signals, in response to the magnetic field, including an RF probe arranged to be located adjacent to the part of the patient;

and a computer and display monitor for decoding and displaying the detected signals;

a table support system mounting the magnet for movement relative to the table in a direction away from the first end of the table from a first position at the table to a second position remote from the table;

the first position of the magnet being arranged such that the part of the patient is positioned in the magnetic field of the magnet while the patient remains in place on the table;

the second position of the magnet being arranged such that the magnet is spaced from the first end of the table by a distance sufficient to allow the surgical team to move around the first end of table and to each side of the table to access the patient and sufficient to allow to allow the surgical team to carry out the surgical procedure;

wherein the magnet wire is formed from magnesium di-boride or Niobium-Titanium.

According to one aspect of the invention which can be used independently of other features set out herein there is provided an apparatus for use in surgical procedures comprising:

an operating room having a floor and walls containing an operating table for receiving a patient for a surgical procedure;

and a magnetic resonance imaging system for obtaining images of a part of the patient at a series of times through the surgical procedure for analysis by the surgical team to allow the surgical team to monitor the progress of the surgery, the magnetic resonance imaging system comprising:

a magnet system comprising a cylindrical magnet of magnet wire defining a cylindrical bore within which a part of the patient is located for placement within high magnetic fields generated by the magnet;

a control system for controlling and varying the magnetic fields;

a radio frequency transmission and detection system for eliciting and detecting from the part of the patient nuclear magnetic resonance signals, in response to the magnetic field, including an RF probe arranged to be located adjacent to the part of the patient;

and a computer and display monitor for decoding and displaying the detected signals;

a table support system mounting the magnet for movement relative to the table in a direction away from the first end of the table from a first position at the table to a second position remote from the table;

the first position of the magnet being arranged such that the part of the patient is positioned in the magnetic field of the magnet while the patient remains in place on the table;

the second position of the magnet being arranged such that the magnet is spaced from the first end of the table by a distance sufficient to allow the surgical team to move around the first end of table and to each side of the table to access the patient and sufficient to allow to allow the surgical team to carry out the surgical procedure;

wherein the magnet has a weight of less than 2 tonne and a floor area in the range 15 to 40 sq feet and typically of the order of 35 sq feet and the magnet is carried on a support system supported from the floor.

According to one aspect of the invention which can be used independently of other features set out herein there is provided a method for use in surgical procedures comprising:

providing an operating room having a floor and walls containing an operating table for receiving a patient for a surgical procedure;

mounting in the room a magnetic resonance imaging system for obtaining images of a part of the patient at a series of times through the surgical procedure for analysis by the surgical team to allow the surgical team to monitor the progress of the surgery, the magnetic resonance imaging system comprising:

a magnet system comprising a cylindrical magnet of magnet wire defining a cylindrical bore within which a part of the patient is located for placement within high magnetic fields generated by the magnet;

a control system for controlling and varying the magnetic fields;

a radio frequency transmission and detection system for eliciting and detecting from the part of the patient nuclear magnetic resonance signals, in response to the magnetic field, including an RF probe arranged to be located adjacent to the part of the patient;

and a computer and display monitor for decoding and displaying the detected signals;

mounting the magnet for movement relative to the table in a direction away from the first end of the table from a first position at the table to a second position remote from the table;

the first position of the magnet being arranged such that the part of the patient is positioned in the magnetic field of the magnet while the patient remains in place on the table;

the second position of the magnet being arranged such that the magnet is spaced from the first end of the table by a distance sufficient to allow the surgical team to move around the first end of table and to each side of the table to access the patient and sufficient to allow to allow the surgical team to carry out the surgical procedure;

wherein the magnet dedicated solely to surgery within the operating room;

wherein the magnet remains in the room at all times;

wherein the magnet is powered off to turn off the magnetic field when in the second position;

and wherein the magnet is cooled by a cooling system which remains on when the magnetic field is powered off.

Magnets attract ferromagnetic material and products built with these materials can become projectiles when close to an MRI magnet and so the moveable magnet should only generate a magnetic field when required for imaging and spend the rest of its time with a magnetic field of around 0 Tesla. The arrangement of the present invention allows the magnetic field to be turned off when the system is not being used for imaging.

Also if the magnet is to be moved, the present arrangement allows that the magnet not contain liquid helium since the use of liquid helium requires a quench pipe to be attached to the magnet because large amounts of helium gas escape very rapidly from the magnet in the event of a quench. Such a large amount of helium gas escaping into the imaging room is dangerous and should not be allowed to occur. Thus the present arrangement avoids the use of an insulated tube attached to the magnet to carry all the helium gas to the exterior of the building should such an event occur. The present arrangement thus allows a system which avoids the use of liquid helium as a coolant.

The quality of the image produced by the MRI techniques is dependent, in part, upon the strength of the magnetic resonance (MR) signal received from the processing nuclei. For this reason an independent RF coil is placed in close proximity to the region of interest of the imaged object, more particularly on the surface of the imaged object, as local coils or surface coils in order to improve the strength of the received signal. These coils receive the signals from the tissue.

The present arrangement allows the use of a surface coil of the type described in U.S. Pat. No. 4,825,162 which shows a surface coil(s) for use in MRI/NMRI imaging and methods related thereto. In the preferred embodiment of that invention, each surface coil is connected to the input of an associated one of a like plurality of low-input-impedance preamplifiers, which minimizes the interaction between any surface coil and any other surface coils not immediately adjacent thereto. These surface coils can have square, circular and the like geometries. This yields an array of a plurality of closely spaced surface coils, each positioned so as to have substantially no interaction with all adjacent surface coils. A different MR response signal is received at each different one of the surface coils from an associated portion of the sample enclosed within the imaging volume defined by the array. Each different MR response signal is used to construct a different one of plurality of different images from each surface coil. These images are then combined, on a point-by-point basis to produce a single composite MR image of a total sample portion comprised of the MR response signals from the entire array of surface coils.

The arrangement of the present invention allows the use of a surface coil as both a transmit and receive coil thus avoiding the use of a conventional body coil used in the majority of high field MRI systems for excitation (called transmit coils) located as a cylindrical structure just inside the bore. These coils take up space in the magnet at a position inside the cylindrical gradient coils and therefore require the magnet bore to be about 10 cm larger in diameter than if this body coil was not present. This larger diameter magnet requires significantly more wire to make a homogeneous magnet resulting in a much heavier magnet making floor loading much more of an issue.

It should be recognized that it is contemplated that the MRI methods of the present invention are to be used in connection with the performance of clinical, diagnostic, interventional, and/or surgical procedures. Thus, it is contemplated and within the skill of those in the art to adapt the MRI methods of the present invention when needed to accommodate the performance of such clinical, diagnostic, interventional, and/or surgical procedures.

However the arrangement herein is designed to be maintained continually in the room to which it is allocated which is typically an operating theater for neurosurgery but can be for other surgeries or can be a diagnostic suite. The MRI magnet in this invention is a 1 Tesla or more magnet made from Magnesium Diboride (MgB2) or Niobium-Tin or Niobium Titanium wire which is a high temperature super conducting wire (Tc is equal to or less than 400K). This high superconducting temperature (Tc=40 K), means that MgB2-based systems can be cooled by modern cryo-cooling devices, without the costly, problematic and hazardous use of liquid helium. The magnet will therefore not need a quench pipe to be connected and so will be much more mobile than any conventional MRI magnet. The magnet can be taken in 10 to 15 minutes to provide a stable homogeneous magnetic field sufficient for high quality MRI imaging. The field is stabilized using control currents which are applied to the magnet wire in response to detection of the field to cause a rapid stabilization.

Therefore the magnet can spend all the time when not imaging at a near zero field and is activated by application of the current to provide the magnetic field when required for imaging. Such a magnet is 70 to 80 cm in internal diameter and weighs less than 2 tonne and so can be moved around a hospital floor using an air cushion or track support system with a standard or conventional floor without extra strengthening being able to accept the necessary loading. The magnet transport system when using an air cushion is constructed such that no particles escape from the skirts designed to stop all particles from entering the hospital atmosphere.

The RF coils will be of the transceiver design with the structure being malleable to form the required actual design to match the body region required to be imaged. The RF transceiver can thus be formed of a flexible structure such as a fabric containing the coils or loops without necessity for any stiffening components to hold the structure at a required location allowing the structure to drape over the imaging area. The structure is arranged to be located at or around the conventional head clamp used in the neurosurgery.

This is not a device normally required to perform whole body imaging but designed to image a particular body region with high resolution and high sensitivity. The coil as a receive coil has many channels, the number depending on the body region to be imaged and the signals from each element will be summed to provide the required image. These receive channels are switched so that they are all connected for the RF transmit process to excite all the hydrogen nuclei in the tissue of interest.

For imaging during normal neurosurgical procedures, the magnet is brought over the patient as has been described previously.

For deep brain stimulation and other procedures on the brain performed by neurosurgeons, the magnet is powered down to zero field and the system is moved so that the magnet is located over the chest and the stomach of the patient. This leaves the head of the patient exposed beyond the end of the magnet remote from the table. The surgeon starts the surgical procedures which require the use of ferromagnetic materials which are attracted to the magnet if at non-zero field. Typically, this is used to form burr holes in the skull using drilling tools. Thus, the surgeon can use conventional tools to carry out the conventional surgical procedures without danger from the attraction to the magnet.

When this part of the procedure is completed, the magnet is turned on and the surgeon can continue the procedure but using only MRI safe devices. The completion of these tasks requires supports in place for the introduction of one or two insertion cannulas or electrodes through the burr holes which have been made in the patient's skull in the first part of the procedure. The trajectory of these are based on stereotactic imaging. When the magnet is at field, relative movement of the patient and magnet is provided such that the head of the patient is received into the homogeneous field of view of the magnet. This can be obtained by the longitudinal movement of the magnet along the table on its moving system. In an alternative embodiment, a telescopic component of the patient table is moved to place the patient's head in the imaging field of view. Images are obtained and fused with pre-operative images which may contain anatomical, functional, and tractography information. These images are used to verify that the trajectory for the electrodes or other probes is correct. The images can also be used to verify that the target has not moved due to brain shift following opening of the skull. If the insertion cannulas or electrodes are not at target then a new trajectory must be calculated so that the implanted electrodes arrive at the true target. Once this is completed, the surgeon implants the electrodes into the brain of the patient and verifies that implanted electrodes are positioned at the target. The insertion cannulas and electrodes can be advanced into the brain with use of robot with or without image guidance. This has been described for the introduction of stereotactic electroencephalogram electrodes but another embodiment of the invention would be to control laser ablation of tumours or other lesions.

The magnet mounted on the mover is preferably be able to rotate 180° about a vertical axis while inside the storage module so that the patient end of the magnet always points towards the OR table in the room being serviced. Preferably the axis is stationary during the movement and located at or adjacent the center of the magnet, but it will be appreciated that the requirement is only that the magnet be rotated so that the axis may not be fixed and may move as rotation occurs and the axis may be located at one end or other location on the magnet.

The 3 key components of the magnet's ability to do 180° rotation are:

-a- Ultra Precise Mover Control: The left and right side tracks are driven by servo motors which during rotation are engaged in the opposite directions causing the magnet to do precise rotation preferably while inside the storage module but in some cases at other locations between the different operation locations. Laser guided sensors are provided which detect any variance from the required accurate rotation and provide motor compensation to maintain accuracy. This allows the magnet to do precise 180° rotation about a fixed vertical axis.

-b- Double Axis CC Design and Flex Tube Guidance which allows the cable carrier to go left into a first operating room or right into a second operating room and also to park in the centre. The centre parked position is guided by a flexible tube that articulates between two positions via a guided tack assembly which has actuated pins that will lock the guide at the different positions. By having the mover enter the required selected room, the flexible tube naturally moves in that direction until it stops at end of the curved track at which point the flexible tube is locked by a controlled actuator pin. The contour of the flex is determined by a fixed arced profile. The flex tube must be locked to keep its curved position when the magnet is traveling in the opposite direction back into the storage module. Just before the magnet is fully inside the storage module, the actuator locking pin releases which allows the flex tube to straighten out and conform to the second position.

-c- Slewing Ring Actuator Control: The Slewing ring mounted to magnet has two parts where the bottom part is rigidly mounted to the magnet and the top part is rigidly mounted to the cable carrier bracket. The two sections of the slewing ring are locked together at either 0° or 180°, or free to rotate by the slewing ring actuator. To allow rotation, the top part is held locked or engaged to the storage module via the actuator while the slewing ring actuator is disengaged to allow magnet rotation. To allow magnet travel, the module actuator is disengaged while the slewing ring actuator is engaged.

The MRI system storage module accesses two adjacent rooms. It travels between the rooms on the servo motor controlled tracked mover. Doors at either side of the storage module allow access to one or the other of the rooms. An interlock is arranged such that only one door can be open at any time.

As explained above, rather than shield the whole room, localized shielding is employed. This can be in the form of a shielding arch mounted to the table where the localized RF shielding arch is a separate component from the table and is stored in the storage module until required. In the storage module the shield sits on a wheeled cart and is stored inside the storage module behind roll up doors on the front of the storage module. This wheeled cart also serves as an alignment/skull clamp positioning tool when preparing the patient for surgery. This positioning tool matches the magnet bore and allows the staff to position the patient prior to surgery to ensure he/she will fit inside the MR prior to it arriving. This will identify any patient to bore interference and saves time when the magnet arrives. This is done as part of patient preparation.

The cart has a fold down flap at its base that engages the front of the table base and ensures the cart is aligned with the magnet travel. The table must be bolted to the floor via the two alignment screws at the rear of the table. This arrangement therefore acts to locate the magnet as it is moved into position relative to the table with the guidance of the magnet movement ensuring that the magnet cannot move inaccurately toward the table with resultant potential collisions or inaccurate final location. The cart carries an alignment ring or bar which is movable on the cart relative to the table.

The OR staff take the tethered bar and sweep the volume that represents the location of the magnet bore when the bore is in place on the table. Any patient/skull clamp contact must result in repositioning of the skull clamp to clear the bar. If the patent clears the bar as it is rotated thus simulating the internal bore of the magnet, it clears the MR bore.

In accordance with another feature of the invention herein there is provided an RF coil design for the intra-operative MRI arrangement.

The transmit coil can be provided as a conventional body coil located inside of the magnet at ISO-center with flare opening at the patient side of the magnet. It will generate quadrature uniform transmit RF B1 field. This design can greatly reduce receive coil weight and improve workflow. However the coils described hereinafter can be used for both transmit and receive functions.

For head imaging, the receive coil comprises an upper and lower coil design: The lower coil is thin-flex design which can be inserted between patient head and Head fixation Device (HFD). The upper coil is Ultra-thin flexible coil which can improve SNR by around 50%. The use of flexible conductors captured in a thin flexible encapsulating materials which allow the structure to be fully flexible to be draped over the face of the patient while lying substantially in contact with all parts of the skin of the patient including forehead, cheeks and chin.

Both upper and lower coil can be integrated with the B0 shim coil which can further improve coil performance To provide efficient sterilization of the coils for use in the surgical environment, both the upper and lower coils can be manufactured so as to be disposable with a disposable medical connector. Alternatively, the coils may be of a reusable type but inserted into a sterilized bag during use.

The coil design uses a plurality of, for example four, coil elements arranged in a row with each partly overlapping the next. Adjacent coil elements 1 and 2, 2 and 3, 3 and 4 are decoupled by using the known overlap method obtained by the partial overlap together with the provision of a shared capacitor coupling the two coil elements. In addition, next neighbor coil elements 1 and 3, 2 and 4 are also decoupled by using shared capacitors connecting the two next neighbour coil elements, Previous coil decoupling only provides decoupling between the adjacent coil element by using shared capacitors between them. There is no decoupling between next neighbor coil elements.

The required preamplifier can be put into a small box on the system cable coupling the coils construction to the system. This allows the coil construction itself to be very thin and lighter.

The differences of the present coil construction relative to previous designs of flex coil is as follows:

-a- the coil design provides effective decoupling between the coil elements by the overlap, direct neighbour decoupling and next neighbour decoupling;

-b- there is provided a cable connection making the coil construction lighter to improve workflow;

-c- the preamplifier can be inside or outside the coil construction making the coil very thin and therefore drapable -d- the coil can be sterilized by being disposable of by using a sterilized bag;

-e- the high flexibility and drape of the coil construction causes the coil to lie closer to the patient and improve SNR up to 50%.

The coil construction should have the following features:
it should not inhibit or restrict the placement and positioning of the head skull to a head fixation device;
it should not restrict the use of navigation systems;
It should generate homogeneous RF field, with great sensitivity inside the desired imaging volume;
it should not interfere or occupy the same space with the designated surgical field;
it should generate a quadrature uniform transmit RF field avoiding interference with the electronics of the surgical robot;
it should control the pattern of specific absorption ratio (SAR) deposition on the human head.
it should be able, by its drapability to be adjusted to a large variety of human heads from a 6 month old infant to a 95% adult male
it should, again by its high drapability, be easily integrated with the Head fixation Device;
it should not disturb the sterile field by being easily sterilized by disposal or by containment in a flexible bag or the required dimensions;
in order to achieve higher SNR, the RF coil must as close to the patient as possible again my use of high drapability The Upper and lower coil size is 31 cm×22 cm. The total coil elements is 8. This size is optimized for the penetration depth of reception from the patient head.

Traditionally, the upper coil is located on top of surgical drape wrapped around the patient head. While these are effective, they have some disadvantages in that the upper RF coil is far away from the patient, which could cause image SNR loses of around 40% to 50%. The coil cable is too long, heavy and very difficult to carry and operate.

According to further aspects of the invention which can be used independently of other features described or defined herein there is provided:

The arrangement described herein can provide one or more of the following advantages:

High Resolution State of the Art image quality.

Cryogen free 1.0 T Superconducting MRI.

No Helium with no quench line required.

Everything contained in one module which can be placed in most ORs:

No dedicated Control Room

No dedicated Equipment Room

Quick installation time—typically less than 3 weeks.

Localized RF shielding—no RF shield room required.

Module has a clean professional appearance with nominal 30 dB acoustic attenuation when the doors are closed.

Includes portable MR compatible OR Table that adapts to the localized RF Shield.

All system components including localized rf shield can be stored inside the storage module so as to reduces OR clutter.

Magnet can be carried on a tracked crawler which distributes load over 0.5 m2 floor area which minimizes floor loading.

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

Figure 1:
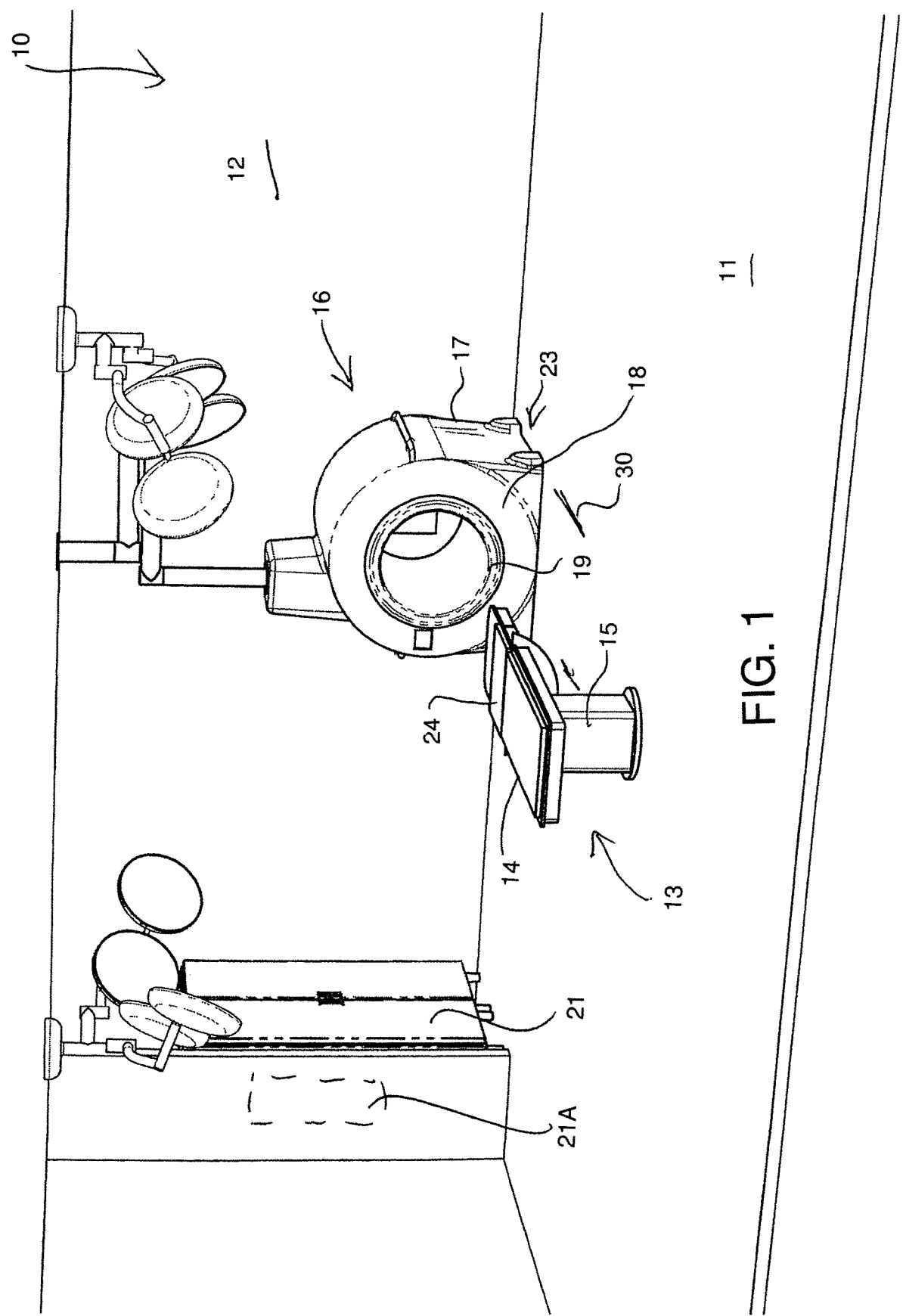
FIG. 1 is an isometric view of an operating theater including an operating table and an MRI imaging system according to the present invention, showing the magnet in a withdrawn position at one wall in the room.

The apparatus for surgical procedures in the embodiment of the Figures includes an operating room 10 having a floor 11 and walls 12 containing an operating table 13 for receiving a patient for a surgical procedure. The table includes a table top 14 on which the patient lies and an upstanding support 15 which is typically adjustable to move the patient to a required position. Constructions of suitable tables are well known in the prior art.

The table cooperates with a magnetic resonance imaging system 16 for obtaining images of a part of the patient at a series of times through the surgical procedure. The images are taken after part of the surgery to assess progress in an analysis by the surgical team to allow the surgical team to monitor the progress of the surgery.

The magnetic resonance imaging system 16 includes a magnet system 17 comprising a cylindrical magnet 18 of magnet wire defining a cylindrical bore 19 within which a part of the patient is located for placement within high magnetic fields generated by the magnet. A control system 21A is provided within the room inside a suitable container or storage module 21 at one side of the room. The control system operates the MRI system and includes a computer and display monitor for decoding and displaying the detected signals using computer operated programs for decoding the various signals to generate images and for operating the RF system, the field of the magnet and other components conventional in this type of system.

Figure 5:
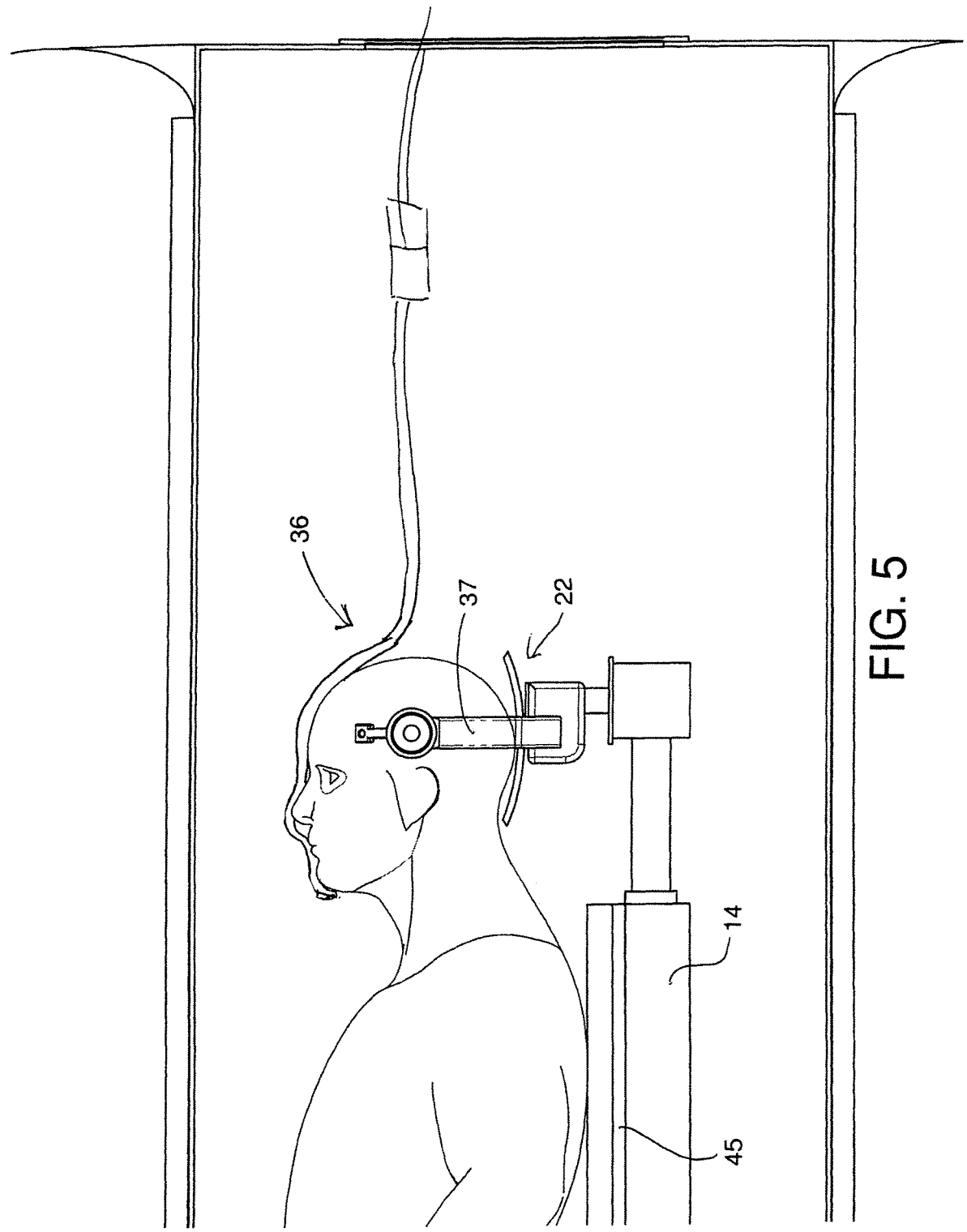
FIG. 5 is a cross-sectional view similar to that of FIG. 3 on an enlarged scale showing the head clamp and RF transceiver.

A radio frequency transmission and detection system 22 is shown in FIG. 5 for eliciting and detecting from the part of the patient nuclear magnetic resonance signals, in response to the magnetic field, including an RF probe located adjacent to the head of the patient.

Figure 2:
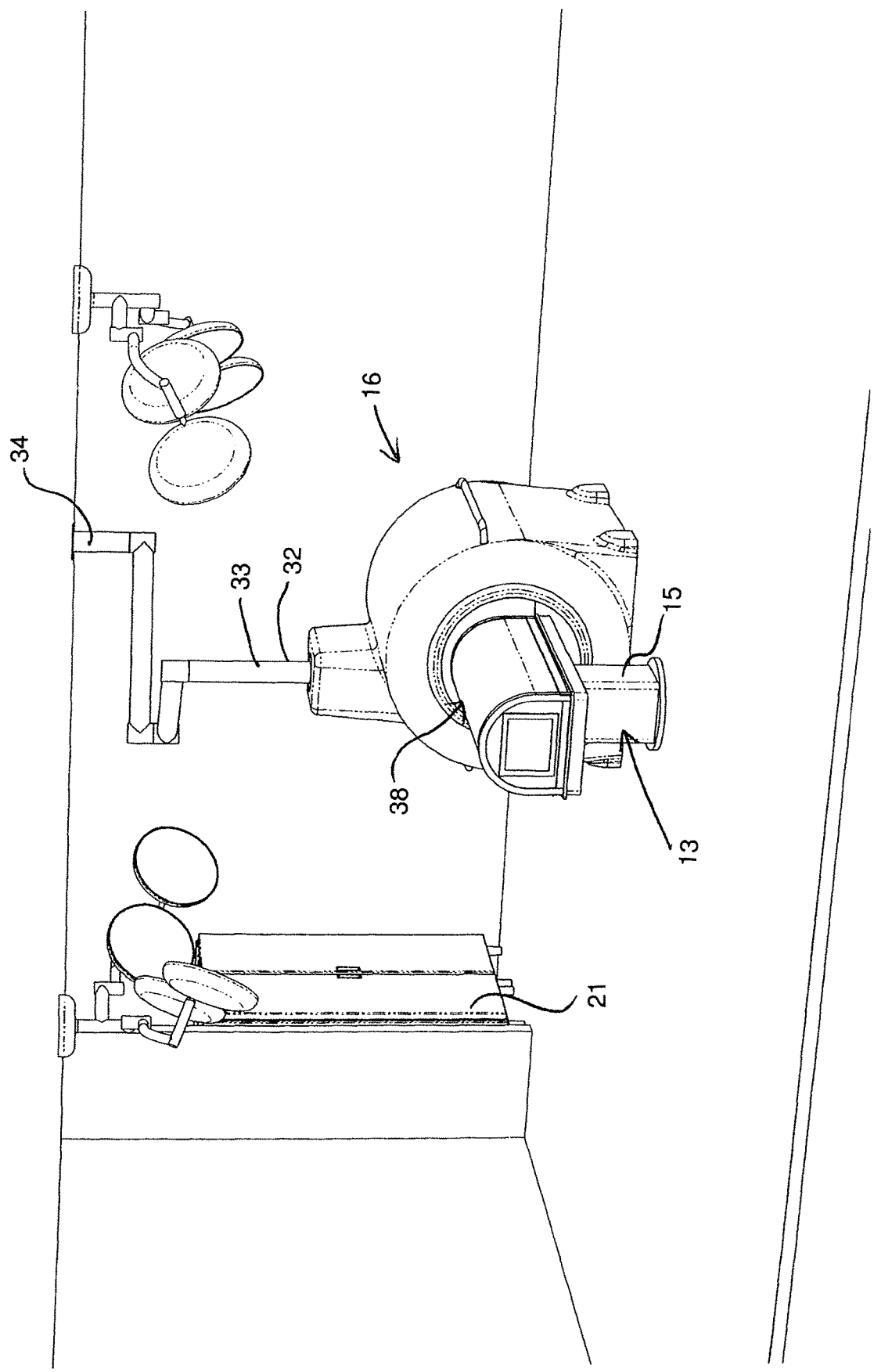
FIG. 2 is a similar isometric view of the same theater with the magnet in the imaging position.
Figure 3:
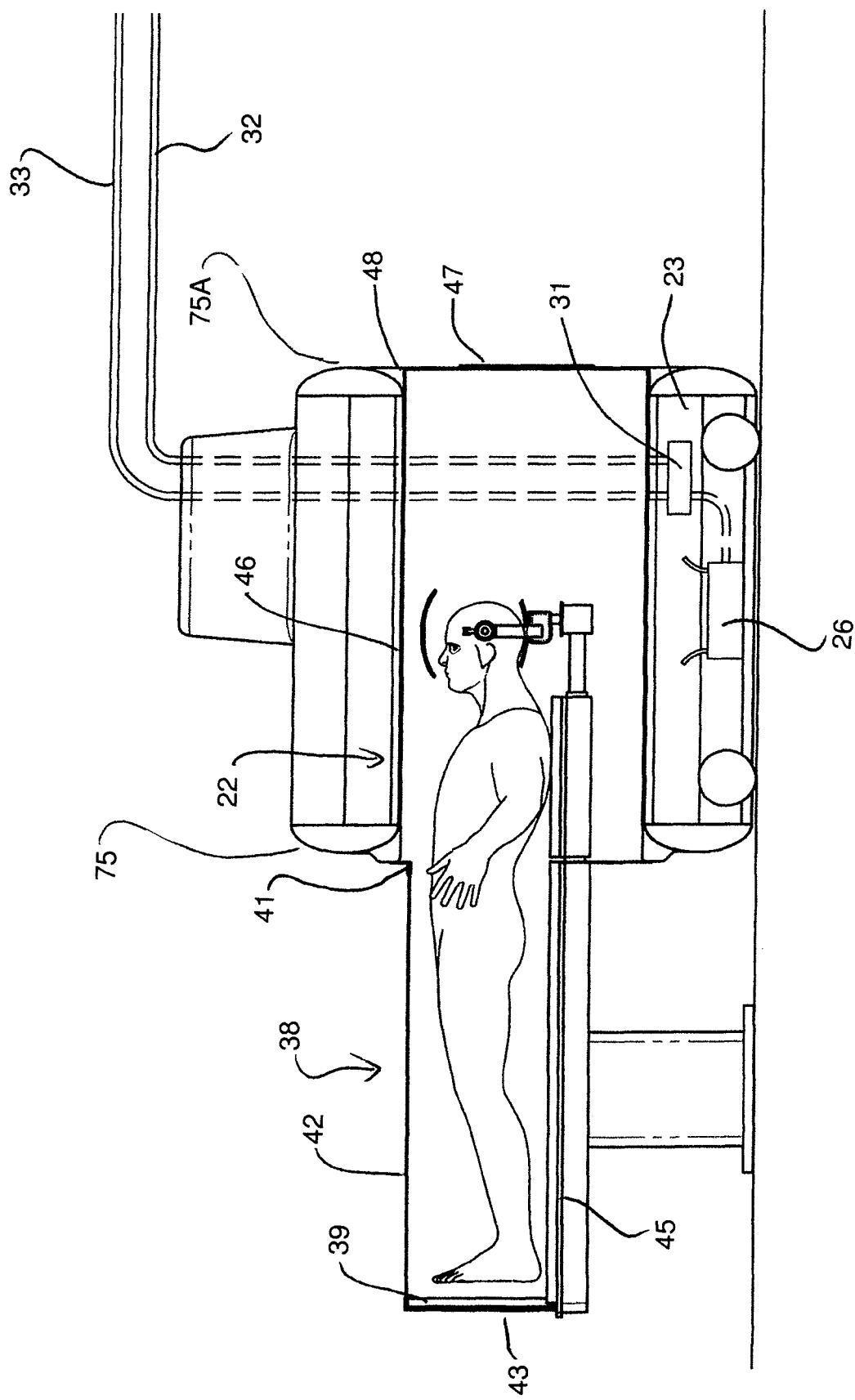
FIG. 3 is a longitudinal cross-sectional view of the table and magnet in the position of FIG. 2.
Figure 4:
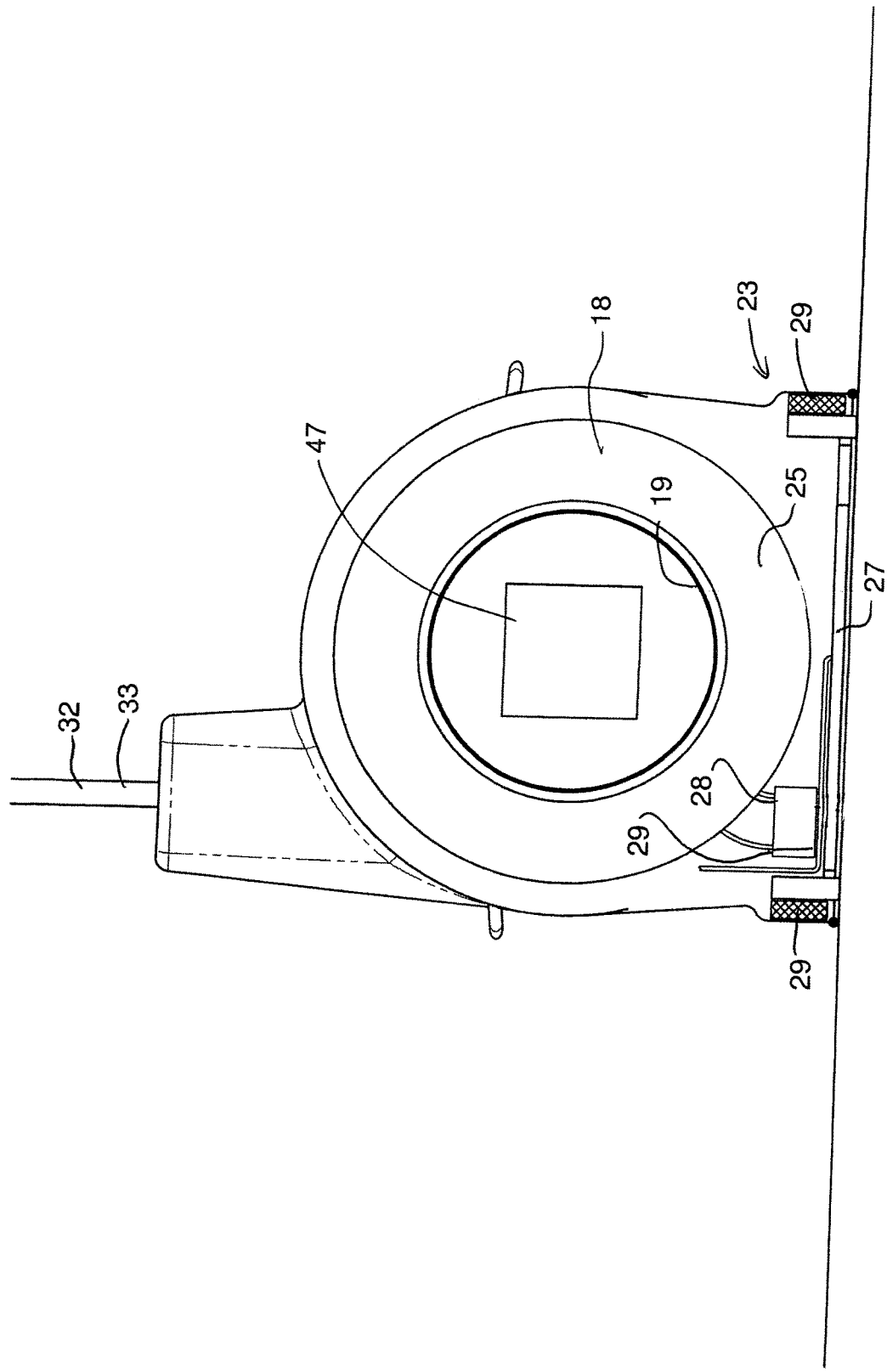
FIG. 4 is a transverse cross-sectional view of the table and magnet in the position of FIG. 2.

The magnet is mounted on a support system 23 mounting the magnet for movement relative to the table in a direction away from the first end 24 of the table from a first position shown in FIG. 2 at or partly over the table to a second position shown in FIG. 1 remote from the table. The second portion is at one wall 12 so as to be well away from the table to ensure the surgeon is not impeded by the presence of the magnet during the surgery.

Thus the first position of the magnet is arranged such that the head, or other part to be imaged, of the patient is positioned in the magnetic field of the magnet while the patient remains in place on the table. Thus the second position of the magnet is arranged such that the magnet is spaced from the first end of the table by a distance sufficient to allow the surgical team to move around the first end of table and to each side of the table to access the patient and sufficient to allow to allow the surgical team to carry out the surgical procedure.

As set forth above, the magnet 17 is designed and arranged as a simple construction of relatively light weight and small size to enable it to be introduced into an existing operating theater and moved between the two positions within the room. Thus the magnet is dedicated solely to surgery within the operating room and remains in the room when used in a single room arrangement. A two room arrangement is described and shown hereinafter.

Thus the magnet has a bore of a small diameter of the order of 60 to 70 cms and typically around 65 cms, so that it is of minimum total diameter thus reducing the length of wrapping wire required. This provides a weight of the order of 1 or 2 tonne, a width of the order of 4 to 5 feet and a length of the order of 5 to 7 feet defining a floor area in the range 15 to 35 sq feet and typically of the order of 20 sq ft.

This small dimension is assisted by the selection of a superconducting material of a suitable material such as magnesium di-boride or Niobium-Tin or Niobium-Titanium which is superconducting at around or below 40 degrees absolute (Kelvin) and hence can be cooled by a cooling system to superconductivity without use of liquid helium.

That is a magnet 17 of this material is cooled by a vacuum cryo-cooling system 25 having a vacuum pump 26 driven by electricity where the pump itself is cooled by a flow of cooling water. Arrangements of this type are previously known to persons skilled in this art so that further explanation is not required.

This weight and dimension of magnet allows the magnet to be carried on an air cushion support system 23 or track system described later supported from the floor of a conventional operating theater applying suitable loads to the structure of the building without additional structural stiffening or supporting components. Thus a load of 2000 to 4000 lbs can be spread over a floor area of 20 to 35 sq feet using an air cushion to spread the load without overloading the existing floor structure. Alternatively the track system described below also can be used to spread the load.

The support system in one example thus comprises an air cushion formed in a chamber 27 covering the base area of the magnet and generated by a fan 28 located within the magnet housing. The chamber has side skirts 29 so as to contain the cushion within the chamber and so as to spread the weight over the entire base area.

The fan is associated with a suitable high efficiency filter system 29 so that it expels and no particles into the chamber 27 so that no contamination can be emitted from the side skirts.

In addition to the support system is guided from the first position to the second position on guide rails 30 where wheels are guided along the rails to ensure that the magnet properly moves between the two positions.

A control processor 31 is provided on the magnet 17 which is operated in response to input controls from the control system 21A so that the magnet is arranged to be powered off to turn off the magnetic field when in the second position. In this way the magnetic field is off during the surgical procedures to avoid interfering with the surgeon's activities and is only turned on for imaging. Also the lift system fan 28 is also off as not required. At the same time, the magnet is arranged such that the cooling system pump 26 remains on powered by the electrical supply 32 and the cooling water 33 from a wall connection 34 when the magnetic field is powered off. The water and electrical supplies are arranged so that there is sufficient slack in the supply cables to allow movement between the first and second positions.

As shown in FIG. 5, the RF probe 22 comprises local transceiver RF coils 36 so as, in some cases, to avoid use of a cylindrical body coil at the bore. These are of the type and construction described hereinafter to avoid the use of a body coil in the bore. These are arranged to wrap around the head clamp 37 and to drape over the head of the patient.

In order to avoid having to shield the whole room, there is provided a shielding structure 38 for excluding RF fields from the RF probe which comprises an arched elongate support frame 39 for extending over the patient and supporting a shielding fabric or screen 40 extending from outside of the feet of the patient at the end of the table top 14 up to the location 41 on the body which enters the bore.

The fabric or screen thus forms an arched upper portion 42 over the patient and a semi-circular end portion 43 closing the end of the arched frame.

The shielding structure 22 further comprises a metal sheet 45 as part of the table top 14 located underneath the patient and extending across the table to the sides of the shielding fabric or screen 40.

The shielding structure 22 comprises a cylindrical shielding layer 46 inside the bore and a hinged door 47 on an end of the bore opposite the table and containing a shielding layer 48.

All of the components of the shielding structure 22 are coupled together to form an integral shield fully surrounding the patient and the RF probe.

The magnet is thus cryogen-free and will attain superconductivity (at less than 40K and nominal 39K) solely by the vacuum pump which requires water cooling located on the magnet. This technology requires the cryocooler and the helium gas compressor which require water cooling. Advancements in vacuum pump technology, also known as a cryo-cooler, that achieves a partial vacuum at 39K which allows the superconductivity using the wire of the material defined herein. No liquid helium is involved because there is no quench pipe to deal with the Liquid:Gas phase change.

The System and PDU cabinets are combined into a single cabinet. The Cabinets listed all have nominal 970 mm/37" depths. This really is not an issue when considering new construction with a dedicated equipment room but when considering retrofits to existing hospitals, space is an issue and it may be necessary to put these cabinets in non-conventional locations (e.g. hallways, viewing rooms, closets, etc). The cabinets can be only 660 mm/26" depth with all cabling out the top, nothing out the back. The approach is to have all cables out from the top. Since space in a hospital is typically at a premium, all equipment to run the MRI system is located in a self-contained storage module of the order of 2 m×4 m×3.2 m tall. The magnet mover cables, equipment and accessories are all located within the module as described in more detail hereinafter.

There is a closed loop system with a water-to-water heat exchanger and an independent circulating pump inside the heat exchanger cabinet. There is a closed loop water cooling system with an inner heat exchanger.

There is a provision for city water bypass (to drain) inside this cabinet but it could be done externally if space is at a premium. In the efforts to minimize external chiller installation costs, the system can use direct hospital chilled water. The city water bypass is a risk mitigator in case the chiller goes down or is serviced. The city water is acceptable for running the helium compressor (vacuum pump). But it cannot be a backup for cooling the gradient coil and gradient amplifier, both of which have a strict requirement of the cooling water such as deionized water. Another option is to use direct hospital chilled water using an internal booster chiller.

The vacuum pump is also known as a cryo-cooler, the industry standard uses the term cryo-cooler, provides a pure vacuum at 0 K; which is almost a vacuum at 3K).

A water-to-water heat exchanger has 2 isolated chambers with solid transfer plates between chambers to do the conductive heat transfer. The MR side of closed loop system always requires deionized water. The chiller side has either chiller water or city water. It is necessary to avoid contamination between the two.

Cabinets require water cooling which is much quieter. Noise is always a concern. The cabinets are in the equipment room or storage module separated from the operator room.

With a cryogen-free magnet a helium compressor is not required The system can compress the heat exchanger and put it in a small cabinet under the gradient amplifier cabinet. The cryogen-free magnet still requires the helium compressor.

There is no conventional penetration panel. The cables for the most part go directly from the storage module to the Magnet and are primarily contained within the cabinet or module. There is a localized RF shield around the patient and inside the MR bore. There are waveguides and a small penetration panel on the OR patient table that will have RF filters associated with the Tx/Rx coils. It plugs directly into this small penetration panel. It requires the use of compact (DB9 sized) RF filters and connectors or fibre optic cables through a waveguide. The system has the all digital receiver design and fiber optic cables so it is not bulky even for a 16-channel system. The transmit cable is copper.

Conventional super conducting MR systems use a fixed cable tray between the (fixed) MR and the equipment cabinets. The system uses a moving cable tray/carrier or Boom scheme to follow the magnet. The system requires nominal 12"/300 mm separation distance between the gradient cables and the RF cable. This is reduced by adding additional shielding around the gradient or RF cables. Also there are some fibre cables which will not be affected by the magnetic fields produced by the high power copper gradient/RF cables. The system requires the large space between gradient cables and RF cables. The system uses fiber cables and we have extra shielding around the gradient cables. The cryogen-free super-conducting electromagnet can be turned on and off by the user requiring roughly 15 minute field stabilization time. There should be magnet charging cables available in addition to the gradient cables in order to charge/discharge the magnet. The magnet charging cables are fixed to the magnet for frequent turn on and off. In the efforts of minimizing cables, the gradients and charging cables are the same cable with a programmable double-pole, single throw switch included depending on the operating current of the magnet and the peak current required for the gradient coil.

Conventional super conducting MR systems have cable sets selected as per the location of the penetration panel (e.g. Siemens: 4 m before/16 m after). They are also made up of cables chosen due to cost and performance. The system herein uses a moveable magnet and needs the most flexible cables available.

The system can in this embodiment us a non-ferrous air pallet that glides around the OR. There is no problem carrying the weight. A 10 lb force with push 5,000 lbs. The MR floor support to be nominal 2,000 lbs which requires nominal 32 SCFM @ 30 PSI. Many manufacturers are available, for example Hoverair. For safety concerns, two people are required to move/steer the MR. Depending on the Cable management system chosen, there are additional moment forces due to the stiffness of the cables that will have to be overcome.

Dust mitigation is obtained by adapting the pallet to include a skirt around the perimeter that catches the exhaust and routes it through a HEPA filter. This would mitigate the OR contamination of dust being blown off the floor. Air Supply is provided by a small rotary screw compressor located above control cabinets which will supply air. Large volume air is required with minimal noise has to be a priority. The system uses an Accumulator (large storage tank) to provide a reserve. There is provided a wheel back up in case air supply fails. The magnet is bolted to this pallet.

There is provided a magnet/table engagement key since the magnet glides around the floor with little resistance so that the magnet cannot bump into the table including a physical "key" that mates/aligns the magnet/table together.

As an alternative, the magnet can have a motorized wheel mechanism associated with a bottom frame. The MR typically sits against the rear wall. When required the user activates a pendent and moves the MR forward to mate with the table. The travel can be controlled by a limit switch on the cable carrier. The alignment can follow a guide such as tape on the floor or a stripe embedded in the flooring. The system includes a table to magnet engagement key to ensure proper table alignment. This eliminates the need of an air supply with expensive screw compressor, holding tank, and noise factor. The nurse does not have to guide it into position. It drives itself with no dust mitigation.

The system has a modular concept where the magnet and cable carrier have to be in the OR. The Equipment rack modules are placed in the OR or remotely located. The desire is to place this self-contained module into any OR requiring a footprint of 4 m×2 m or in some cases 3.6 m×1.5 m and 3 m tall as shown below. With the roll-up doors shut, the module will be as quite as possible. The overall control of the system is through the HMI (Human Machine Interface) which is located on the front of the module. The standard outputs are to the hospital's DICOM/PACS system via the internet or directly wired to the OR boom monitors. The standard inputs to the module are:

Electrical power (480V 3Ø)
Hospital Chilled water (supply and return)
City water (supply and drain)
Hospital Air (minor)

In regard to managing the cables between cabinets and magnet, there are two options:

Boom arm vs. rolling cable tray. Note that the cable management may add a moment force to the magnet transport solution which has to be overcome/managed. Also, we have to provide any additional shielding to adequately compensate for the required cable separation distances if required.

Cable Carrier: This is mounted adjacent to the magnet and inside the storage module and follow the magnet as it travels. While parked, everything is hidden inside the storage module. Limit switches on the cable carrier determine magnet position. 400 mm/16" width is allotted for this cable carrier.

The arched localized RF antenna system and RF Table Base Flange (RF penetration panel) are in contact with the RF gasket. There is an alignment key to make sure the magnet aligns with the table. The RF gasket also serves as an Anti-Collision Sensor that will stop the magnet's travel if a collision with the patient table/skull clamp occurs.

An MR compatible OR table is provided capable of accepting a MR compatible Mayfield-like skull clamp with standard OR table features and suitable for adaptation to a localized RF shield (see previous section). The table is of a non-ferrous metal beneath the removable arched localized RF antenna system which is pinned onto RF table base flange which is electrically isolated from the rest of the table. Two large waveguides are included at the rear of the table to provide access through the shield to the patient. Everything to the left that is the back section onwards of the localized RF antenna system, which mates with the magnet, is non-ferrous plastic. The OR Table also has to service non-neuro cases. The patient can lay on the table feet first or head first. An extension is provided that allows the magnet to access all parts of the body.

A spine board is provided which is a fiberglass rigid board that lays on top of the table that allows non-neuro procedures to be performed. This provides a distributed load over the entire table. A smaller spine extension can plug into holes for the skull clamp. Additional supports can include side slides or a kick-down support floor pole. All weight is on the back section axis.

The table can have a sliding MR table surface which is more typically in keeping with what a typical diagnostic table would do. Since the system includes a custom RF bore liner, this can include side rails which the table slides on. This table surface is not moved during a OR surgery since all the patient hook-ups have to move also which is too dangerous. The table is moved before the surgery starts and the hook-ups are in place. Lift, Roll and Trendellenberg functions are present in the base section of the table which are electrically isolated from the fiberglass sliding top section.

Part of the Neuro solution is to have a MR-Compatible Skull Clamp. Radiolucent Mayfield-style skull clamps are available off the shelf. They have been deemed not MR compatible since the carbon-fibre structure induces eddy-currents in high field MR systems (>1.5 T). However, as the present system uses a magnet at around 1 tesla, so that an off-the-shield carbon radiolucent skull clamp will work. This skull clamp is part of the RF Tx/Rx Head coil which has to fit around it.

Turning now to FIGS. 6 to 10, there is shown a modified embodiment using a track mover. This includes a support system 50 supported from the floor 51 mounting the magnet for movement relative to the table.

The support system comprises first and second endless drive tracks 52, 53 each along or adjacent a respective side of the magnet and carried on an undercarriage 54 of the magnet. Each track is wrapped around end guide members 55, 56 and each has a lower track run 57 engaging the floor. A drive Each of the drive tracks is driven by a servo motor 59 driving through a gear box 58 a sprocket 60 engaging the track. The servo motor avoids the use of hydraulics and ensures very accurate control of the movement of the tracks. The servo motors are controlled by a drive system (not shown) so that when the drive tracks are driven simultaneously this provides accurate forward and rearward movement. When the tracks are driven differentially this will provide a turning movement either to change direction of movement or to rotate around a vertical axis. The drive system uses sensors 61 and 62 located on the undercarriage to detect a beam or line or mark, such as a laser beam generated by sources 63 and 64 on the table at the floor 51 to direct the tracks to carry the magnet to a required location. When moving toward the table it is important that the magnet moves accurately along the line of the table to avoid collisions with table or patient. Thus sensors on each side and at front and rear of the magnet ensure directional movement along the required direction and immediately detects any deviation or twisting from a required path. In order to provide accurate guidance there are at least two transversely spaced guide lines either at the floor or at table height which are detected by sensors at a front and rear of the magnet.

As described hereinafter, in the storage module, rotation of the magnet about a fixed center vertical axis is obtained by driving the drive tracks in accurately opposed directions.

Figure 6:
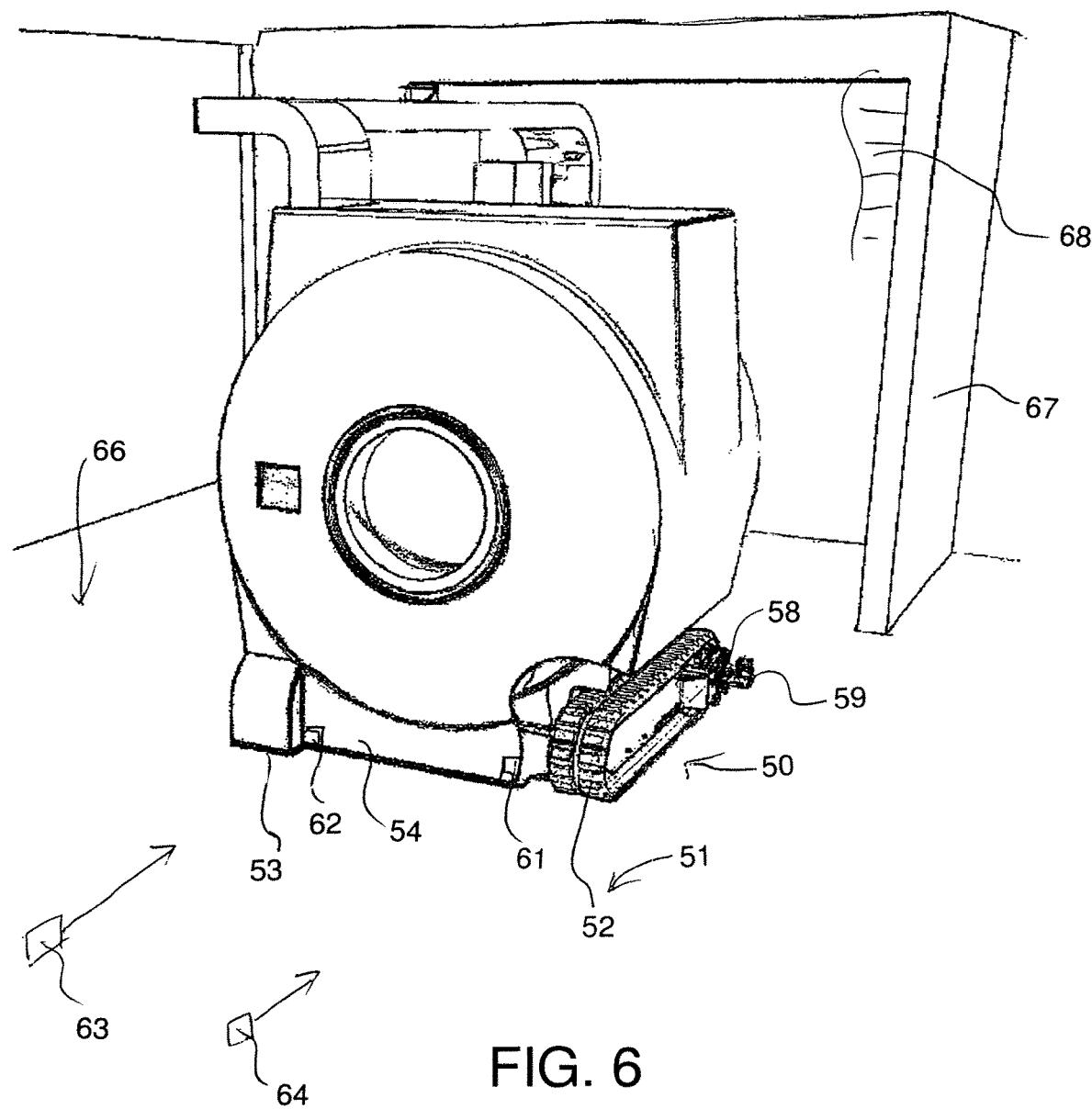
FIG. 6 is an isometric view of an operating theater including a second embodiment of magnet for an MRI imaging system magnet according to the present invention, showing the magnet moving into the room from a storage module.

In one embodiment shown in FIG. 6 there is a single magnet mounted in a single room 66 where the magnet retracts to a storage module 67 when not required. The storage module has a front open face which can be closed by a rolling door 68 when the magnet is stored.

Turning now to the arrangement in FIGS. 13 and 16 to 18 there is provided two adjacent operating rooms 70 and 71 each having a floor and walls containing an operating table (not shown) for receiving a patient for a surgical procedure. Between the rooms is provided a storage module 72 with roll doors 68 at each end for storing the magnet. The module 72 is located between the rooms where the magnet is movable on its drive tracks or other transport system into the storage module 72 and from the storage module to the table each of the rooms.

In order to service both rooms, the magnet is rotatable as shown at 73 on the drive tracks in the storage module about a vertical axis 74 so that a front end 75 of the magnet moves into the room at the forward end for cooperating with the table.

Figure 16:
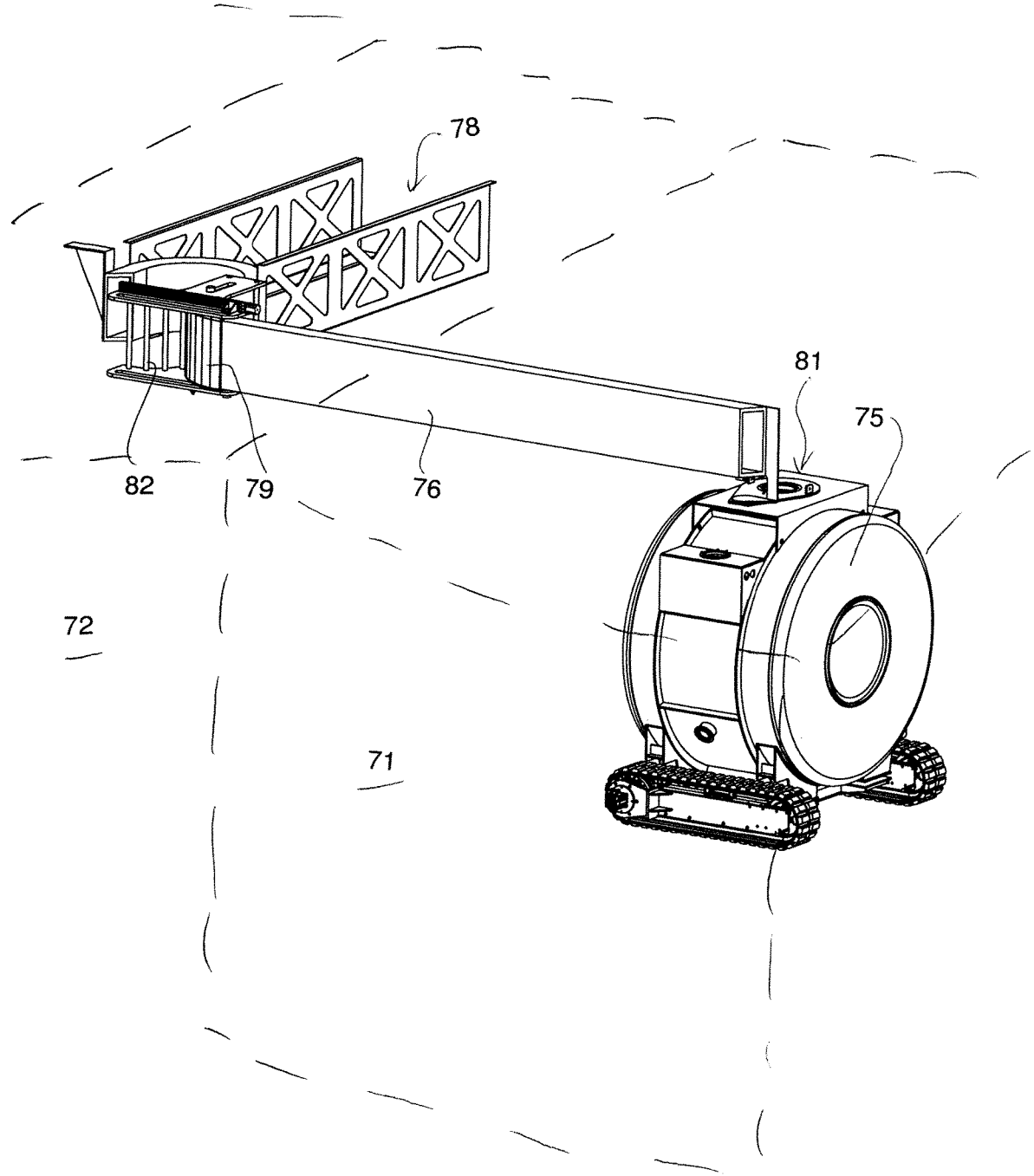
FIGS. 16, 17 and 18 show a cable carrying system for use with the magnet of FIG. 6 in the rooms of FIG. 13.
Figure 17:
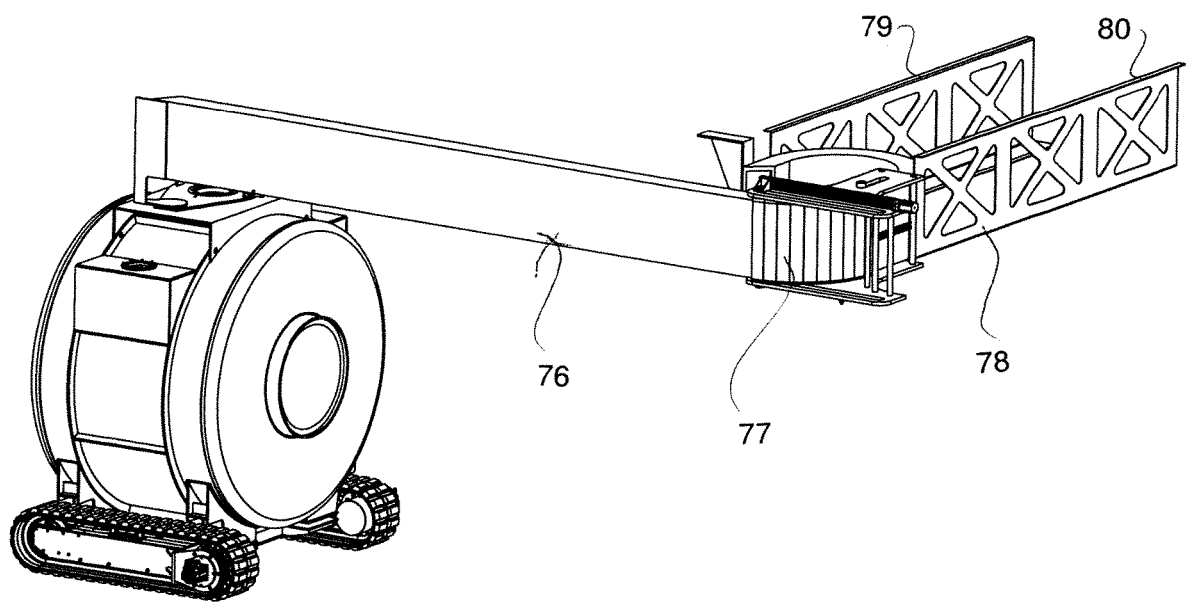
Figure 18:
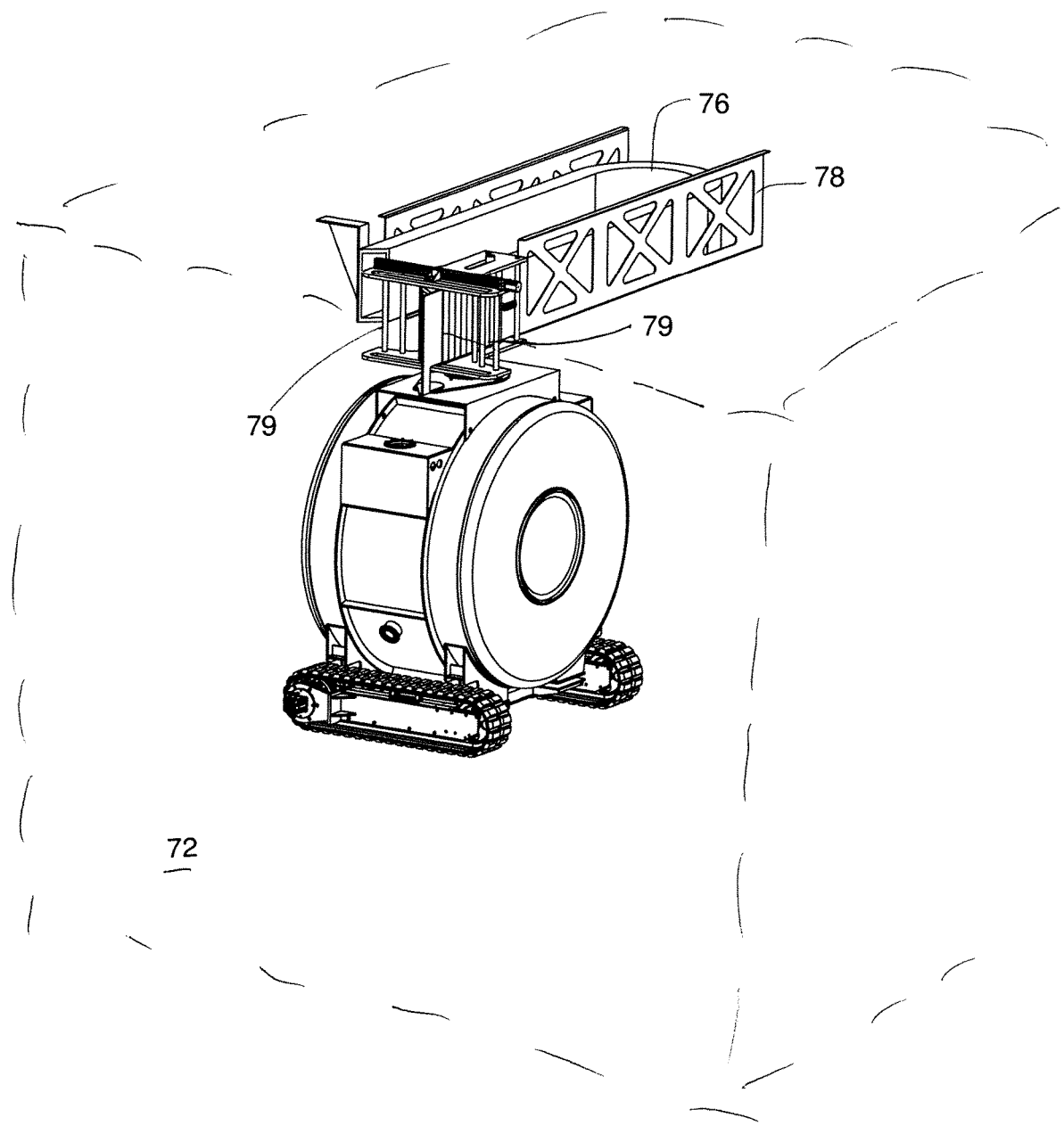

As shown in FIGS. 16 to 18 there is provided a cable guide system 76 which carries electrical and cooling water cables together with the signal cables from the storage module 72 to the magnet. The cable guide system comprises a rolling support 77 which can move to an extended position shown in FIGS. 16 and 18 into the selected room and can roll or fold into a receptacle 79 which can be received into a receptacle 78 defined by two parallel walls 79 and 80. The cable support thus remains in a horizontal position extending generally from the top of the module 72 to the top of the magnet as the magnet moves to carry the cables at this horizontal position. The folding or rolling action allows the cable support to be retracted into the receptacle when the magnet is retracted into the module. Underneath the outer end of the cable support at the magnet is provided a slew ring arrangement by which the rotation of the magnet in the storage module is accommodated. This combination of extendible cable support and slew ring allows feeding of cables from the storage module to the magnet when in each of the rooms and allows the magnet to rotate in the module between the rooms. The rotation of the magnet is driven by the tracks moving in opposite directions and the slew ring helps to maintain that movement accurately around the fixed vertical axis underneath the receptacle in the module.

The left and right side tracks are thus driven by servo motors which during rotation are engaged in the opposite directions causing the magnet to do precise rotation preferably while inside the storage module but in some cases at other locations between the different operation locations. Laser guided sensors are provided which detect any variance from the required accurate rotation and provide motor compensation to maintain accuracy. This allows the magnet to do precise 180° rotation about a fixed vertical axis.

The cable carrying system is defined by the double axis CC design and flex tube guidance which allows the cable carrier to go left into a first operating room or right into a second operating room and also to park in the centre. The centre parked position is guided by a flexible tube that articulates between two positions via a guided tack assembly which has actuated pins that will lock the guide at the different positions. By having the mover enter the required selected room, the flexible tube naturally moves in that direction until it stops at end of the curved track at which point the flexible tube is locked by a controlled actuator pin. The contour of the flex in the cable guide as it rolls around into the receptacle is determined by a fixed arced profile 82. The cable guide which is rollable must be locked at the profile 82 to keep its curved position when the magnet is traveling in the opposite direction back into the storage module as the magnet movement pushes against the cable carrier and forces it back into the receptacle. Just before the magnet is fully inside the storage module, the actuator locking pin releases which allows the cable guide to straighten out and conform to the second position.

The slew ring mounted between the magnet and the cable guide magnet has two parts where the bottom part is rigidly mounted to the magnet and the top part is rigidly mounted to the cable carrier bracket. The two sections of the slew ring are locked together at either 0° or 180°, or free to rotate by the slew ring actuator. To allow rotation, the top part is held locked or engaged to the storage module via the actuator while the slew ring actuator is disengaged to allow magnet rotation. To allow magnet travel, the module actuator is disengaged while the slew ring actuator is engaged.

The MRI system storage module thus accesses the two adjacent rooms. It travels between the two rooms on the servo motor controlled tracked mover. Doors 67 at either side of the storage module allow access to one or the other of the rooms. An interlock is arranged such that only one door can be open at any time.

Figure 11:
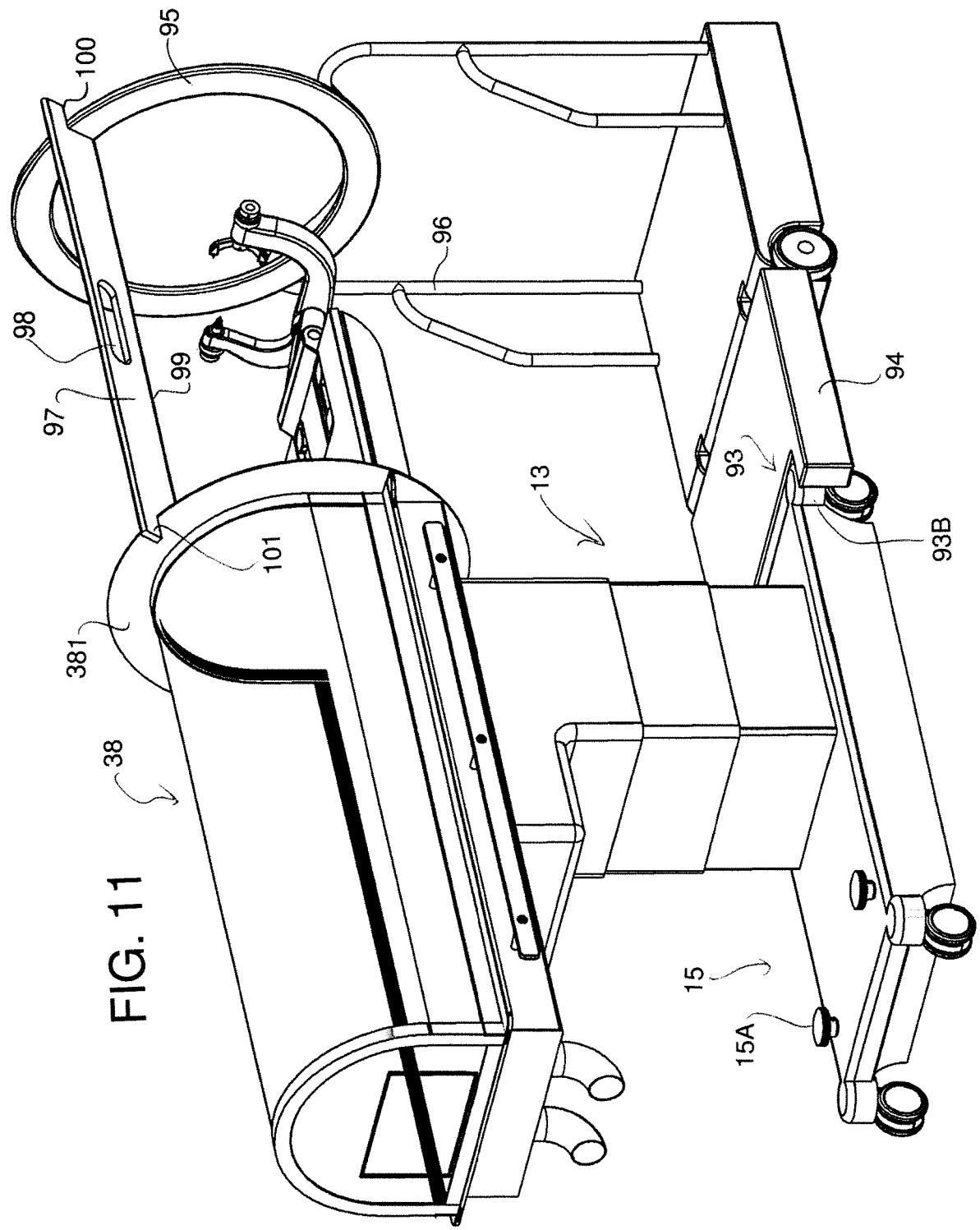
FIG. 11 is an isometric view showing a transportation and alignment cart for use with the table of FIG. 7 prior to the movement of the magnet up to the table.
Figure 12:
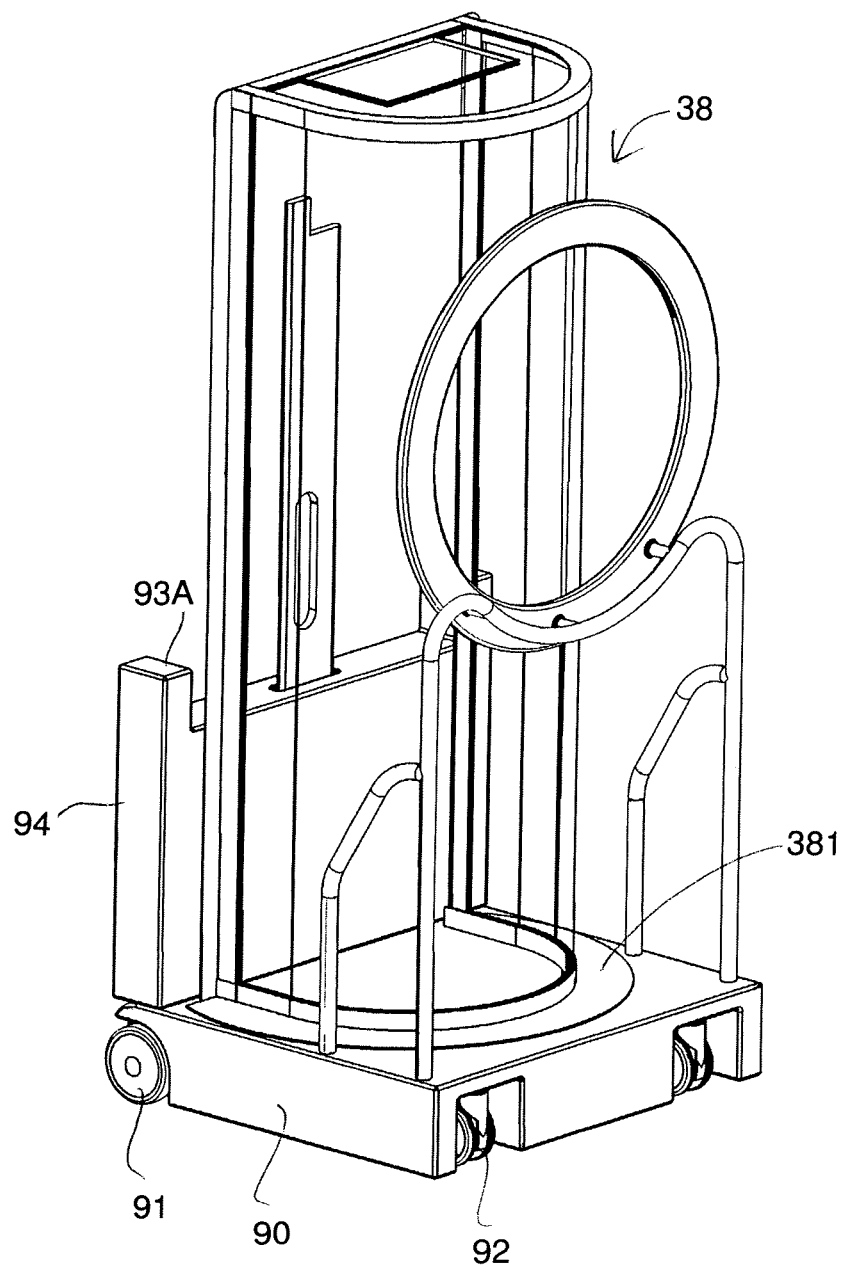
FIG. 12 is an isometric view of the cart of FIG. 11 in a transport position.
Figure 13:
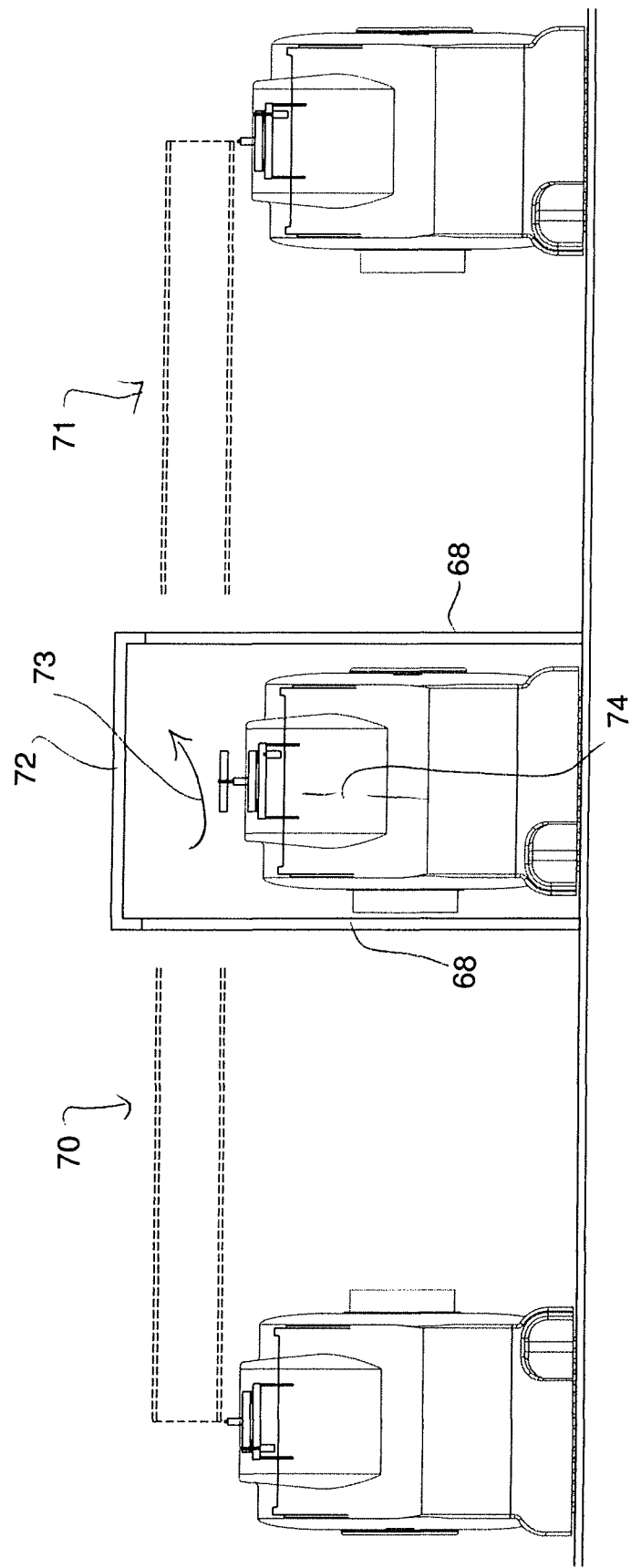
FIG. 13 is an elevational view of the magnet of FIG. 6 movable between two operating rooms with a storage and operational module located therebetween.

Turning now to FIGS. 11 and 12 there is shown an alignment device for properly locating the patient on the table relative to the position of the cylindrical bore when the magnet is moved into its required location at the table. Thus there is provided a location device for simulating a location of a bore of the magnet when moved to the table. This is shown in stored position prior to use in FIG. 12 and in operating position in FIG. 11.

The location device comprises a movable cart 90 mounted on rear ground wheels 91 and on steerable front ground wheels 92 which can thus be moved into position at the magnet. A locating system 93 comprises cooperating components 93A on the cart and 93B on the table which locate the cart at the table in fixed predetermined position. The cart includes a folding extension portion 94 which can be retracted into storage as shown in FIG. 12. Thus with the base 15 of the table 13 fixed to the floor by fastening components 15A and the cart fastened to the table by the coupling 93, the cart is held fixed in position relative to the floor so as to define a location for the magnet 16 to be brought up onto the table.

The movable cart 90 provide a support base for receiving the shielding assembly 38 previously described. Thus when not in use and not attached to the table, the shielding structure can be moved to storage on the cart. The shielding structure carries an end guide ring arranged in use to butt up against the front face of the magnet when the magnet is brought up to an imaging position. The ring 381 thus defines a first guide ring which, when the shielding structure is attached to the table as shown in FIG. 11, acts to simulate a location of the front end of the bore of the magnet when the magnet is in the first imaging position.

The cart carries a second guide ring 95 carried on rails 96 upstanding from the base of the cart. The cart is thus fixed relative to the table and therefore relative to the ring 381 fixed on the table. The ring 95 is fixed relative to the cart and thus relative to the table. The ring 95 is located relative to the cart and thus the table so as to simulate a location of the rear end of the bore of the magnet when the magnet is in the first imaging position These two rings are therefore supported in coaxial position at relative locations which simulate the front and rear of the bore of the magnet when the magnet is brought to its imaging position.

An elongate bar member 97 with a handle hole 98 and an inner edge 99 is provided which has a length spanning the first and second guide rings. Each end has a shoulder 100, 101 sitting on an outside edge of the respective guide disk. The inside edge 99 of the bar is arranged so that rotation of the elongate bar member 97 around the first and second rings forms an imaginary cylindrical surface which accurately matches the actual cylindrical surface of the bore when the magnet is in the first imaging position. Thus the inside edge of each of the rings matches the bore at its ends and the inside edge 99 follows the inside edge of the rings so that the inside edge lies in the imaginary cylinder matching the bore at each position around the rings. Prior to the magnet being brought into position, with the patient and associated components such as the head clamp and imaging coils in position on the table it will be appreciated that any impingement of the bar member on any part of the patient or patient support predicts an unacceptable impingement of the magnet when the magnet is finally brought into imaging position. Thus the bar acts as a prior detection system for ensuring the patient properly positioned and if necessary repositioned, before the magnet is actually moved.

As explained above, rather than shield the whole room, localized shielding is employed. This can be in the form of a shielding arch mounted to the table where the localized RF shielding arch is a separate component from the table and is stored in the storage module until required. In the storage module the shield sits on the wheeled cart and is stored inside the storage module behind roll up doors on the front of the storage module. This wheeled cart also serves as an alignment/skull clamp positioning tool when preparing the patient for surgery. This positioning tool matches the magnet bore and allows the staff to position the patient prior to surgery to ensure he/she will fit inside the MR prior to it arriving. This will identify any patient to bore interference and saves time when the magnet arrives. This is done as part of patient preparation.

The cart 90 has a fold down flap 94 at its base that engages the front of the table base and ensures the cart is aligned with the magnet travel. The table must be bolted to the floor via the two alignment screws 15A at the rear of the table. This arrangement therefore acts to locate the magnet as it is moved into position relative to the table with the guidance of the magnet movement ensuring that the magnet cannot move inaccurately toward the table with resultant potential collisions or inaccurate final location. The cart carries an alignment ring or bar which is movable on the cart relative to the table.

The OR staff take the tethered bar and sweep the volume that represents the location of the magnet bore when the bore is in place on the table. Any patient/skull clamp contact must result in repositioning of the skull clamp to clear the bar. If the patent clears the bar as it is rotated thus simulating the internal bore of the magnet, it clears the MR bore.

The system can be used for imaging many parts of the body of the patient but is primarily designed for imaging the head and when arranged to do so includes a conventional head clamp 37 with side pins 371 acting to clamp the head of the patient between the pins. The pins are carried on a bracket 372 attached to a support 373 mounted on an extension portion 141 of the table top 14.

Figure 14:
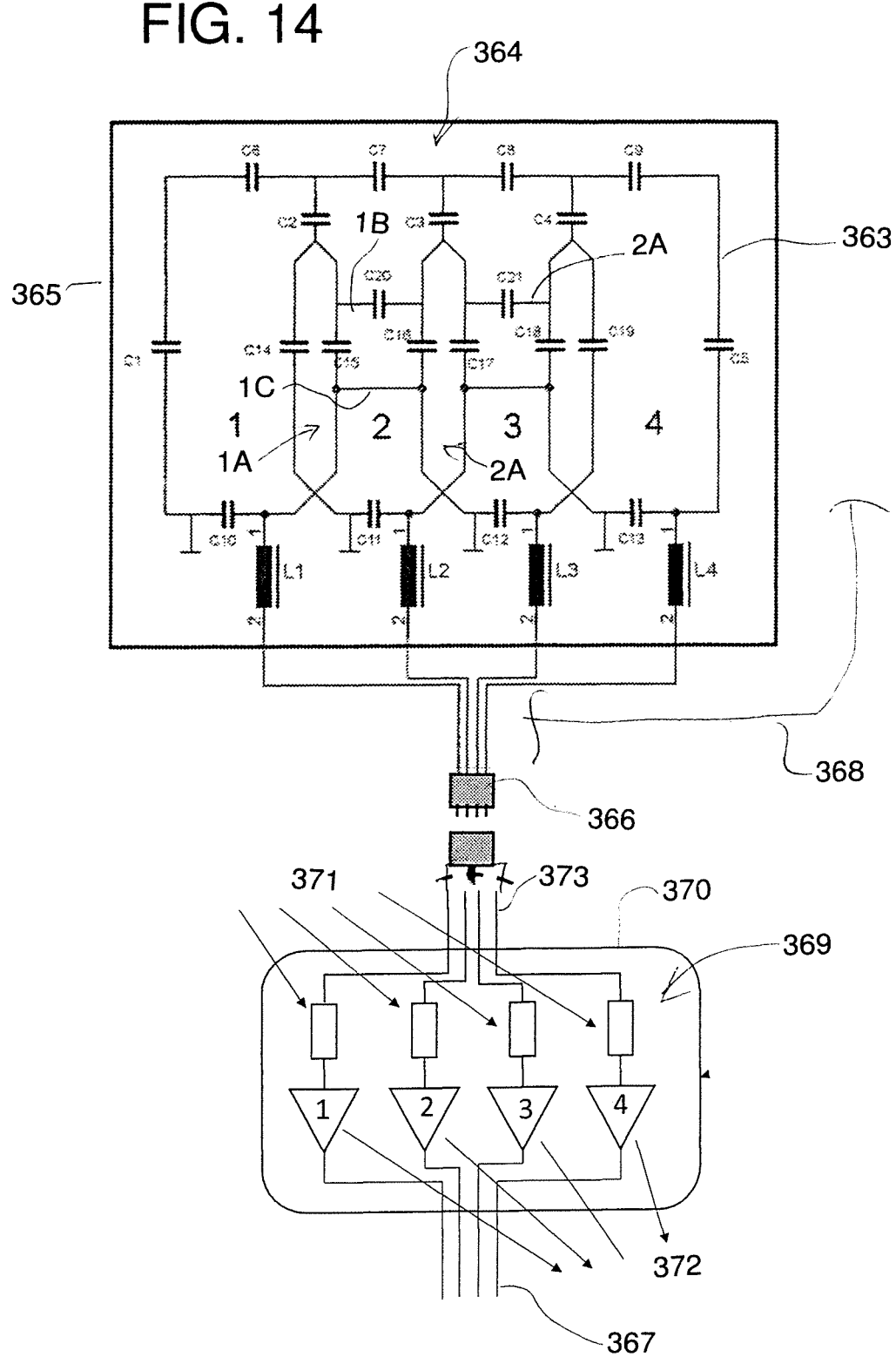
FIG. 14 is a plan view of the RF coil of FIG. 5 showing a series of coil loops connected to a communication cable for connection to the computer control system.
Figure 15:
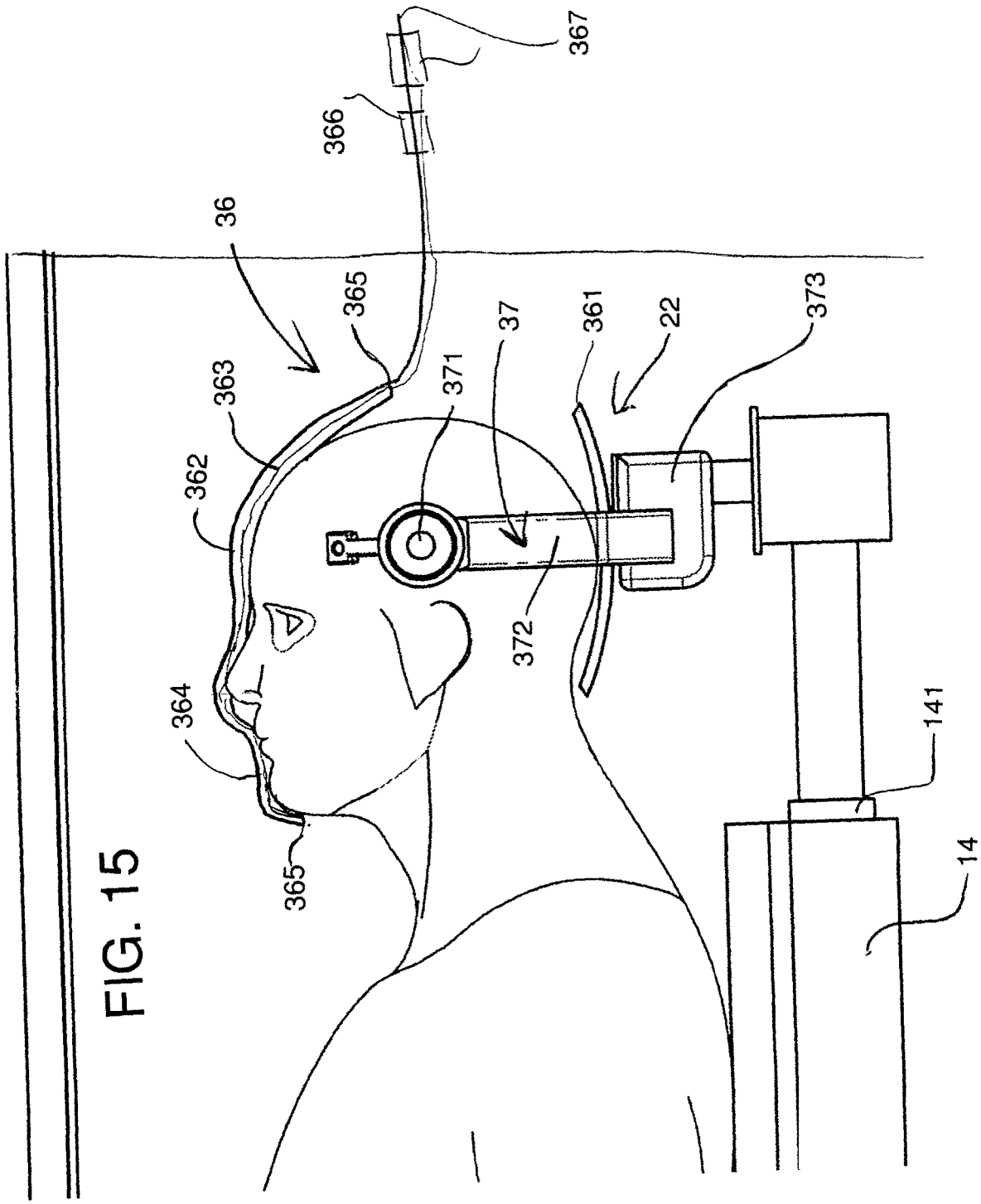
FIG. 15 is a cross-sectional view of the RF coil of FIG. 5 showing the RF coil in cross-sectional view.

The coil construction 36 is best shown in FIGS. 14 and 15 and comprises a lower RF coil assembly 361 mounted on or within the head clamp 37 underneath the head of the patient. The lower coil 361 can be rigid or flexible and is preferably flexible to take up a required position underneath the head but on top of the bracket 371. If it is flexible it can be moved to lie closely adjacent the lower part of the head. The coil construction can be of the same types and arrangement as the coil structure of the top coil assembly 362 described below.

The RF probe comprises therefore the upper RF coil assembly 362 arranged to be engaged with the head of the patient as shown in FIG. 15. Also in view of the fact that the coil remains in place during the surgical procedures, at least the RF upper coil assembly is in a sterilized condition allowing it to be used in the surgical procedure;

The sterilized RF upper coil assembly 362 is draped over the head of the patient with the flexibility of the upper coil assembly causing it to conform at least in part to the shape of the parts of the head against which the assembly is engaged. That is, the upper coil assembly is draped into direct contact with the head of the patient and has sufficient flexibility so as to conform without application of force holding it in place. The upper coil construction comprises a flexible conductor arrangement 363 encapsulated in a flexible plastics material 364 which directly engages the head of the patient and conforms thereto. Thus both the upper and lower surfaces of the coil are formed from the plastics material with the conductor contained within the material. The material can be cast in place around a formed conductor assembly or can be formed form two overlying layers containing the conductor therebetween. The flexible plastics material is formed from a material which is MR compatible in that it can tolerate the magnetic field and does not create artifacts in the image. The flexible plastics material 364 has a thickness less than 5.0 mm. The flexible plastics material has a flexibility so that when applied over the head of the patient, edges 365 of the upper coil depend below the head under their own weight without application of additional force.

In order to provide efficient sterilization for use in the surgical procedure, at least the upper coil assembly is manufactured so as to be disposable and includes a disposable medical connector 366 for connection to a signal cable 367 to the computer control system. The connector 366 includes a part at the end of the cable so that the cable is used repeatedly while the relatively minor component defined by the conductors 363, the covering plastics and the connector 366 are arranged for one time disposable use.

As an alternative, in order to provide efficient sterilization for use in the surgical procedure, at least the upper coil assembly 363 is inserted into a sterilized bag 368 during use for reuse of a previously used upper coil assembly. Each surgical procedure therefore uses a separate sterilized bag into which the coil assembly 363 is inserted during use.

The upper coil assembly 363 includes a preamplifier 369 which is mounted in a container 370 on the signal cable 367 connected to the computer control system so that the coil construction 363 itself is very thin and light as the cable including the connector 366 and the preamplifier 369 are not part of the draped conductor as shown in FIG. 15.

The preamplifier 367 includes for each conductor connected to a respective coil element 1, 2, 3 or 4 of the coil construction 363 a respective phase shift circuit 371 between the respective conductor 373 and the respective preamplifier 372. Each conductor 373 is connected to a respective coil element 1, 2, 3, 4 by a respective inductor L1 to L4 connected to the coil elements on the other end, with the values of the components selected to make a phase shift for each coil element equal to half wave length at the working frequency of the MR system.

It has been found that the flexibility and drape of the upper coil assembly causes the coil to lie closer to the patient and improve SNR up to 50% and to allow it to be adjusted to a large variety of human heads from a 6 month old infant to an adult male.

The head transmit coil can be provided as a conventional body coil located inside of the magnet at ISO-center with flare opening at the patient side of the magnet. It will generate quadrature uniform transmit RF B1 field. This design can greatly reduce receive coil weight and improve workflow. Alternatively the transmit function can be carried out using the upper and lower coil construction 361, 362.

For head imaging, the receive coil comprises an upper and lower coil design: The lower coil is thin-flex design which can be inserted between patient head and Head fixation Device (HFD). The upper coil is Ultra-thin flexible coil which can improve SNR by around 50%. The use of flexible conductors captured in a thin flexible encapsulating materials allows the structure to be fully flexible to be draped over the face of the patient while lying substantially in contact with all parts of the skin of the patient including forehead, cheeks and chin.

Both upper and lower coil can be integrated with the B0 shim coil which can further improve coil performance To provide efficient sterilization of the coils for use in the surgical environment, both the upper and lower coils can be manufactured so as to be disposable with a disposable medical connector. Alternatively, the coils may be of a reusable type but inserted into a sterilized bag during use.

As shown in FIG. 14, at least the upper coil assembly uses a plurality of coil loops or elements 1, 2, 3 and 4 arranged in a row with each partly overlapping the next. This arrangement is generally known and used to provide decoupling between the individual coils.

That is, adjacent pairs of coil loops 1, 2 and 2, 3 etc are decoupled by the partial overlap 1A, 2A etc together with a shared capacitor C2, C3 coupling the two coil loops of the pair. Also next neighbor coil loops 1, 3 and 2, 4 are also decoupled by using shared capacitors C20, C21 connecting the two next neighbour coil loops.

In this way the upper coil assembly comprises at least first, second and third coil loops 1, 2, 3 arranged in a row where each coil loop 1, 2, 3 includes a plurality of capacitors at spaced positions therearound. Thus coil 1 has capacitors C1, C2, C15 and C10. Coil 2 has capacitors C14, C7, C16 and C11 with each coil loop partly overlapping the next so that the first is partly overlapped with the second and the second is partly overlapped with the third;

Thus the first and second coil loops are decoupled by the partial overlap thereof together with the provision of a first additional decoupling capacitor C2, C3 shared on a common portion of the first and second loops. Also the second and third coil loops 2, 3 are decoupled by the partial overlap 2A thereof together with the provision of a second additional decoupling capacitor C3 shared on a common portion of the second and third loops. Finally, the first and third coil loops 1, 3 are also decoupled by using third additional capacitor C20 in a connecting conductor 1B between the first and third coil loops. Also there is provided a second connecting conductor 1C between the first and third loops.

As shown there is also provided a fourth coil loop 4 arranged in the row where the third and fourth coil loops 3, 4 are decoupled by the partial overlap thereof together with the provision of a third additional decoupling capacitor C4 shared on a common portion of the third and fourth loops and where the second and fourth coil loops 2, 4 are also decoupled by using fifth additional capacitor C21 in a connecting conductor 2A between second and fourth coil loops.

The coil design uses a plurality of, for example four, coil elements arranged in a row with each partly overlapping the next. Adjacent coil elements 1 and 2, 2 and 3, 3 and 4 are decoupled by using the known overlap method obtained by the partial overlap together with the provision of a shared capacitor coupling the two coil elements. In addition, next neighbor coil elements 1 and 3, 2 and 4 are also decoupled by using shared capacitors connecting the two next neighbour coil elements, Previous coil decoupling only provides decoupling between the adjacent coil element by using shared capacitors between them. There is no decoupling between next neighbor coil elements.

Figure 7:
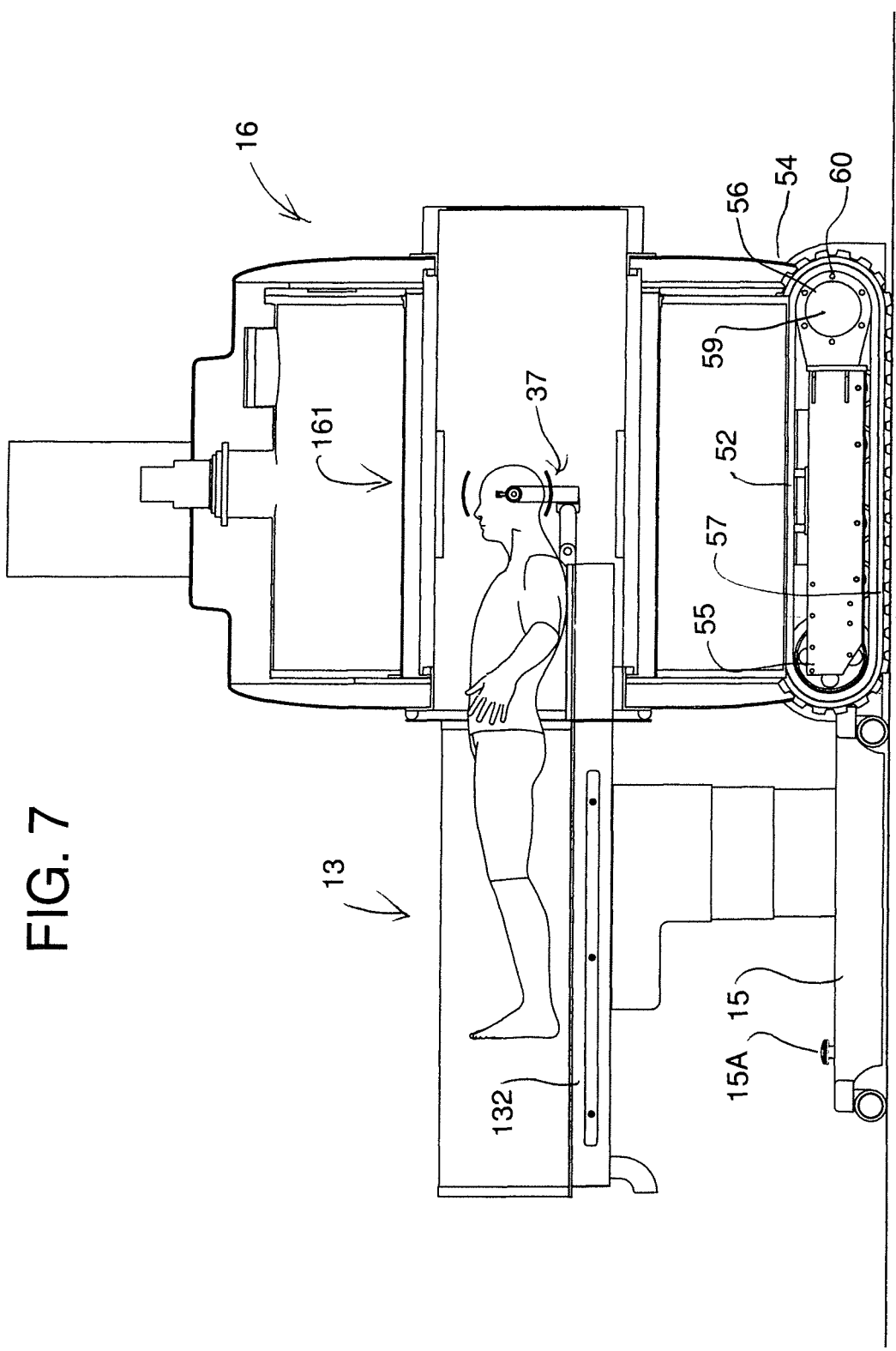
FIGS. 7, 8, 9 and 10 are cross-sectional views showing the magnet of FIG. 6 in different positions relative to an operating table enabling the imaging system using the magnet and table to be used in a functional imaging method where operations by the surgeon can be carried out using both ferromagnet and non-ferromagnetic tools.
Figure 8:
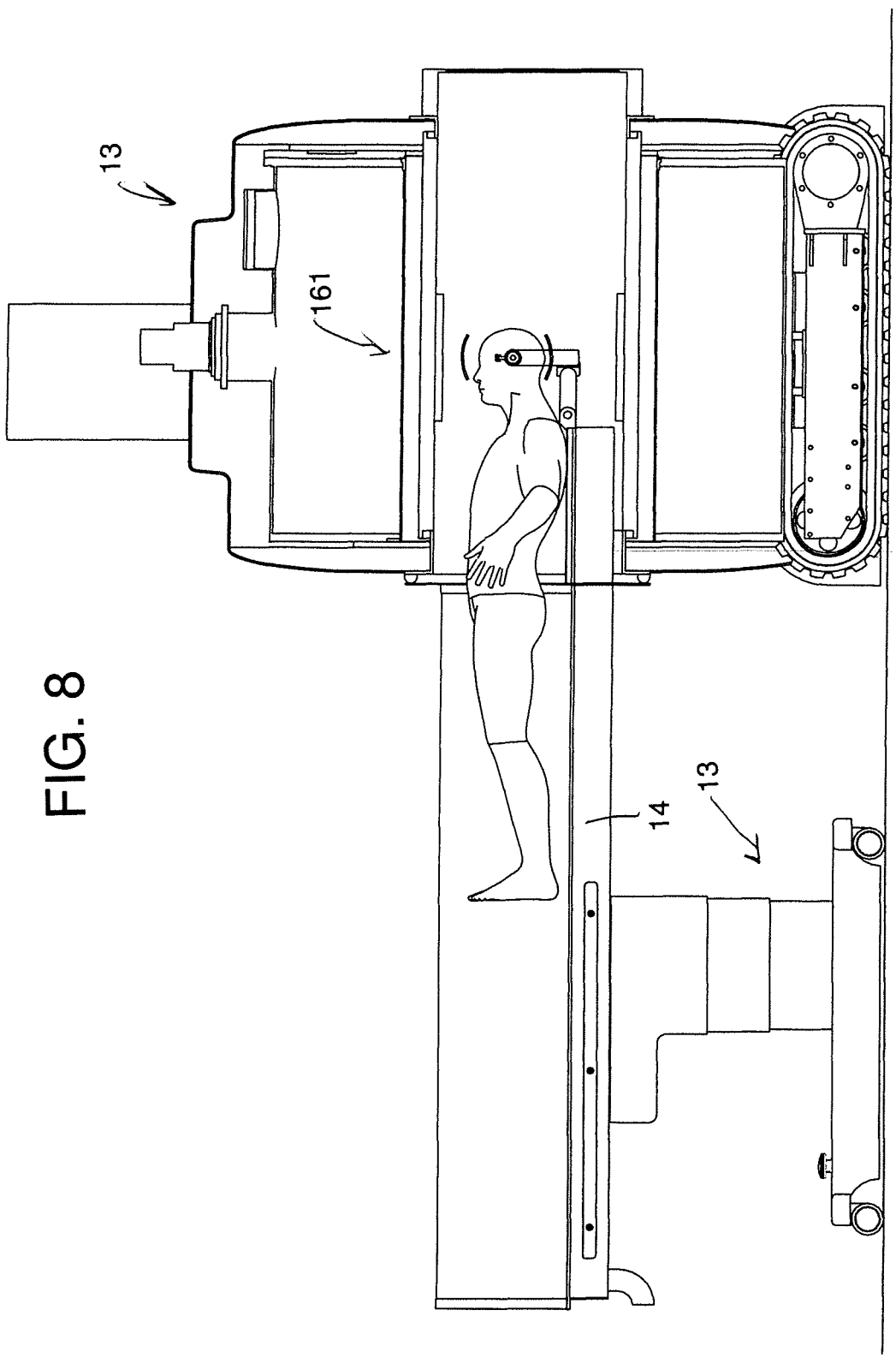
Figure 9:
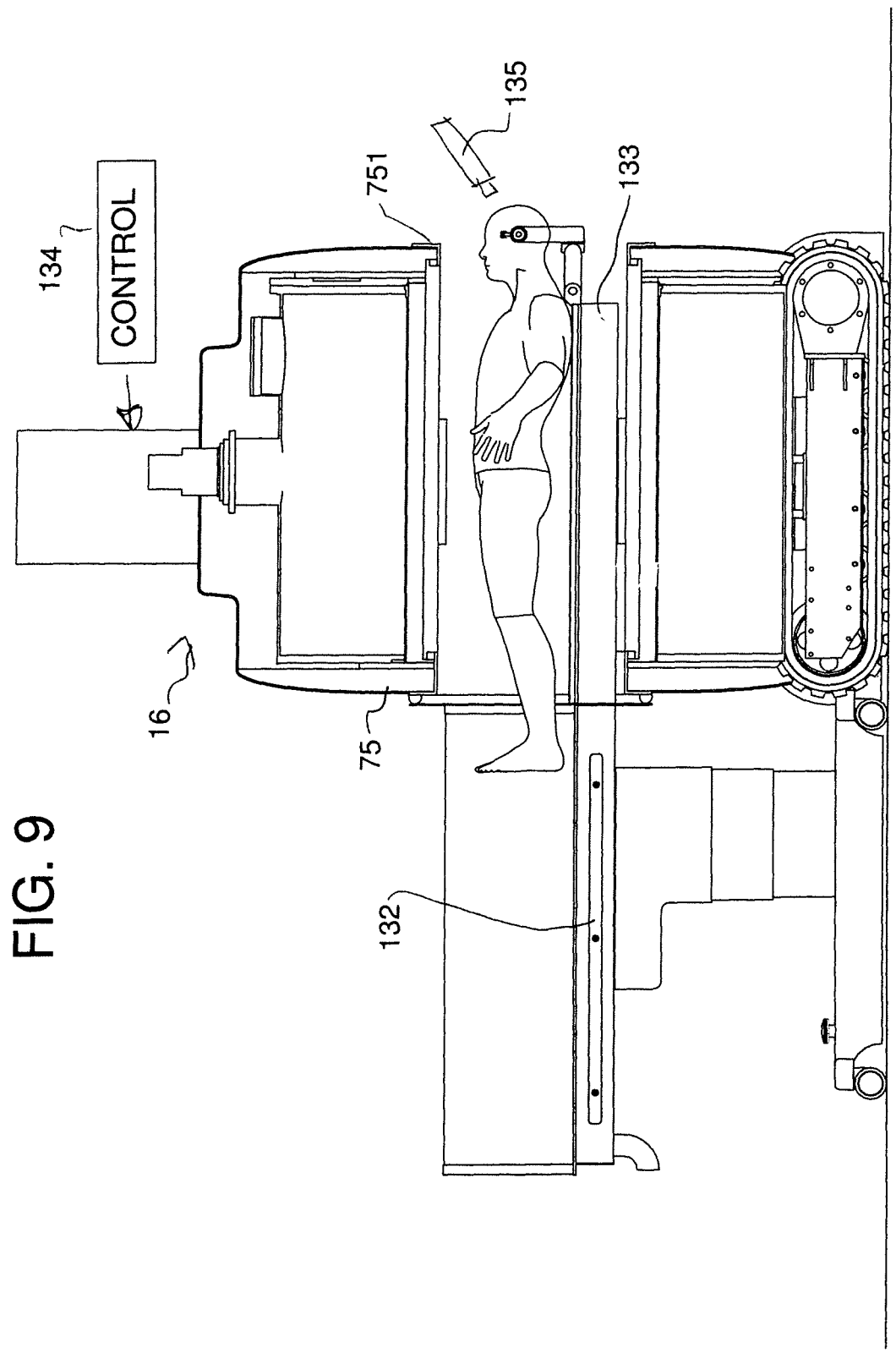
Figure 10:
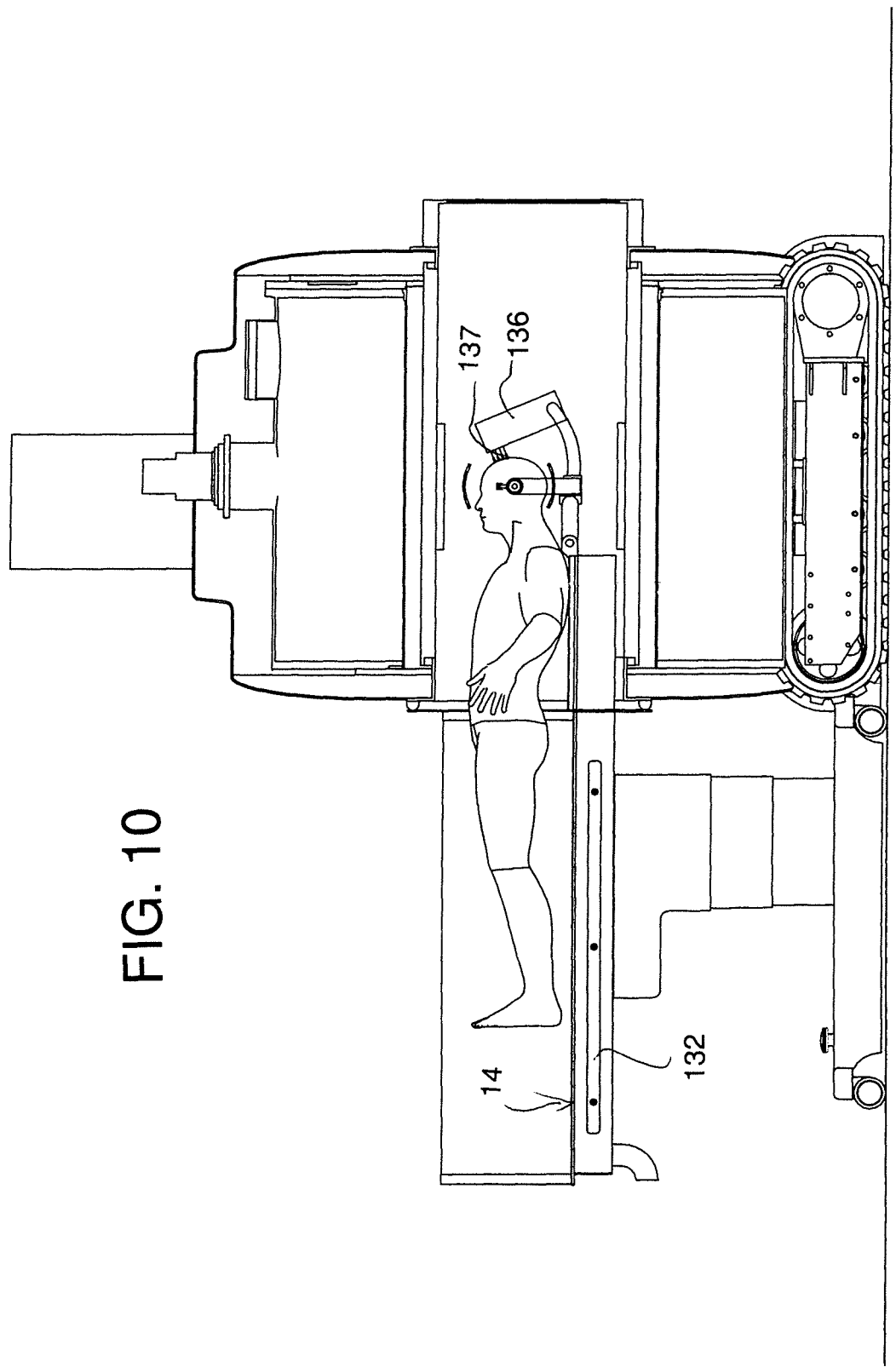

The arrangement herein as best shown in FIGS. 7 to 10 can be used in a functional MRI operation where, in a first position shown in FIG. 7, the table 13 and magnet 16 locate the head of the patient to be imaged on the head clamp 37 within an imaging area 161 of the magnet and in a second position shown in FIG. 9 the head of the patient is exposed beyond a rear or remote end 751 of the magnet 16 so as to accessible for an operative procedure.

In order to move between these positions, the magnet and table are mounted for relative movement in a direction longitudinal of the table from the first imaging position to the second non-imaging position;

As shown in FIG. 9, the magnet is movable along the table so that the patient end is moved to a position closely adjacent a base of the table with the table cantilevered into the magnet and the table is extended by a slide portion 133 on a track 132 longitudinally into the magnet in the second position.

In the second position shown in FIG. 9, the magnet is powered off by a control 134 to turn off the magnetic field when in the second position to enable surgical procedure to be carried out in the second position using ferromagnetic tools 135 such as drills.

After the part of the patient is exposed in the second position of FIG. 9, the part is moved by the relative movement to the first position of FIG. 7 for imaging and the power applied to the magnet by control 134, while non-ferromagnetic tools 137 are provided for additional surgical procedures to be carried out in the first position. The tools 137 can include a robot guidance system 136 within the magnet for carrying out the additional surgical procedures. The tools 137 can include a probe at the first position for insertion into the head of the patient guided by the imaging such as for DBS.

For deep brain stimulation and other procedures on the brain performed by neurosurgeons, the magnet is powered down to zero field at FIG. 9 and the system is moved so that the magnet is located over the chest and the stomach of the patient. This leaves the head of the patient exposed beyond the end of the magnet remote from the table. The surgeon starts the surgical procedures which require the use of ferromagnetic materials which are attracted to the magnet if at non-zero field. Typically, this is used to form burr holes in the skull using drilling tools. Thus, the surgeon can use conventional tools to carry out the conventional surgical procedures without danger from the attraction to the magnet.

When this part of the procedure is completed, the magnet is turned on and the surgeon can continue the procedure but using only MRI safe devices. The completion of these tasks requires supports in place for the introduction of one or two insertion cannulas or electrodes through the burr holes which have been made in the patient's skull in the first part of the procedure. The trajectory of these are based on stereotactic imaging. When the magnet is at field, relative movement of the patient and magnet is provided such that the head of the patient is received into the homogeneous field of view of the magnet. This can be obtained by the longitudinal movement of the magnet along the table on its moving system. In an alternative embodiment, a telescopic component of the patient table is moved to place the patient's head in the imaging field of view. Images are obtained and fused with pre-operative images which may contain anatomical, functional, and tractography information. These images are used to verify that the trajectory for the electrodes or other probes is correct. The images can also be used to verify that the target has not moved due to brain shift following opening of the skull. If the insertion cannulas or electrodes are not at target then a new trajectory must be calculated so that the implanted electrodes arrive at the true target. Once this is completed, the surgeon implants the electrodes into the brain of the patient and verifies that implanted electrodes are positioned at the target. The insertion cannulas and electrodes can be advanced into the brain with use of robot with or without image guidance. This has been described for the introduction of stereotactic electro-encephalogram electrodes but another embodiment of the invention would be to control laser ablation of tumours or other lesions.

The invention claimed is:

1. Apparatus for imaging in surgical procedures comprising:
an operating room having a floor and walls containing an operating table for receiving a patient for a surgical procedure;
and a magnetic resonance imaging system for obtaining images of a part of the patient at a series of times through the surgical procedure for analysis by the surgical team to allow the surgical team to monitor the progress of the surgery, the magnetic resonance imaging system comprising:
a magnet system comprising a cylindrical magnet of magnet wire defining a cylindrical bore within which a part of the patient is located for placement within high magnetic fields generated by the magnet;
a control system for controlling and varying the magnetic fields;
a radio frequency transmission and detection system for eliciting and detecting from the part of the patient nuclear magnetic resonance signals, in response to the magnetic field, including an RF probe arranged to be located adjacent to the part of the patient;
and a computer and display monitor for decoding and displaying the detected signals;
a support system supported from the floor mounting the magnet for movement relative to the table in a direction longitudinally of the table from a first imaging position at the table to a second non-imaging position;
wherein the support system comprises first and second endless drive tracks each along or adjacent a respective side of the magnet, each wrapped around end guide members and each having a lower track run engaging the floor;
the drive tracks being driven simultaneously for forward and rearward movement and being driven differentially for turning movement.

2. The apparatus according to claim 1 wherein each of the drive tracks is driven by a servo motor driving through a gear box a sprocket engaging the track.

3. The apparatus according to claim 1 wherein rotation of the magnet about a vertical axis is obtained by driving the drive tracks in opposed directions.

4. The apparatus according to claim 1 wherein there is provided a guidance system having line sensors responsive to one or more guide lines aligned parallel to a longitudinal direction of the table.

5. The apparatus according to claim 4 wherein the guide lines are formed by a laser.

6. The apparatus according to claim 4 wherein there are at least two transversely spaced guide lines.

7. The apparatus according to claim 4 wherein there are line sensors at a front and rear of the magnet.

8. The apparatus according to claim 1 wherein the magnet has a weight of less than 2 tonne and a floor area in the range 15 to 40 sq feet and preferably of the order of 35 sq ft.

9. The apparatus according to claim 1 wherein there are provided two adjacent operating rooms each having a floor and walls containing an operating table for receiving a patient for a surgical procedure and a storage module for the magnet located between the rooms where the magnet is movable on the drive tracks into the storage module and from the storage module to the table each of the rooms.

10. The apparatus according to claim 9 wherein the magnet is rotatable on the drive racks in the storage module about a vertical axis.

11. The apparatus according to claim 9 wherein there is provided a cable guide system which carries cables from the storage module to the magnet where the cable guide system allows said rotation of the magnet in the storage module and allows feeding of cables from the storage module to the magnet when in each of the rooms.

12. The apparatus according to claim 11 wherein there is provided a receptacle in the storage module for the cable guide system when retracted from the rooms.

13. The apparatus according to claim 1 wherein there is provided a location device for simulating a location of a bore of the magnet when moved to the table, the location device comprising:
 a movable cart which can be moved into position at the magnet;
 the movable cart carrying a first guide ring which simulates a location of a rear end of the bore of the magnet when the magnet is in the first imaging position;
 a second guide ring arranged to be mounted on the table for engaging a front end of the bore of the magnet when the magnet is in the first imaging position;
 and an elongate bar member spanning the first and second guide rings so that rotation of the elongate bar member around the first and second rings forms an imaginary cylindrical surface which matches the actual cylindrical surface of the bore when the magnet is in the first imaging position so that impingement of the bar member on any part of the patient or patient support predicts an unacceptable impingement of the magnet on said part of the patient.

14. The apparatus according to claim 13 wherein the movable cart includes a locating coupling which engages the table to locate the cart at a predetermined location relative to the table and supports the first ring so that, when at the predetermined location, the first ring is located at a position simulating the rear end of the magnet.

15. The apparatus according to claim 13 wherein the second ring is mounted on a shielding assembly which is attached to the table.

16. The apparatus according to claim 15 wherein shielding assembly is removable from the table and is mounted on the movable cart for transport.

17. Apparatus for imaging in surgical procedures comprising:
 an operating room having a floor and walls containing an operating table for receiving a patient for a surgical procedure;
 and a magnetic resonance imaging system for obtaining images of a part of the patient at a series of times through the surgical procedure for analysis by the surgical team to allow the surgical team to monitor the progress of the surgery, the magnetic resonance imaging system comprising:
 a magnet system comprising a cylindrical magnet of magnet wire defining a cylindrical bore within which a part of the patient is located for placement within high magnetic fields generated by the magnet;
 a control system for controlling and varying the magnetic fields;
 a radio frequency transmission and detection system for eliciting and detecting from the part of the patient nuclear magnetic resonance signals, in response to the magnetic field, including an RF probe arranged to be located adjacent to the part of the patient;
 and a computer and display monitor for decoding and displaying the detected signals;
 a support system supported from the floor mounting the magnet for movement relative to the table in a direction longitudinally of the table from a first imaging position at the table to a second non-imaging position;
 wherein there are provided two adjacent operating rooms each having a floor and walls containing an operating table for receiving a patient for a surgical procedure and a storage module for the magnet located between the rooms where the magnet is movable into the storage module and from the storage module to the table each of the rooms and wherein the magnet is rotatable in the storage module about a vertical axis.

18. The apparatus according to claim 17 wherein there is provided a cable guide system which carries cables from the storage module to the magnet where the cable guide system allows said rotation of the magnet in the storage module and allows feeding of cables from the storage module to the magnet when in each of the rooms.

19. The apparatus according to claim 17 wherein there is provided a receptacle in the storage module for the cable guide system when retracted from the rooms.

20. Apparatus for imaging in surgical procedures comprising:
 an operating room having a floor and walls containing an operating table for receiving a patient for a surgical procedure;
 and a magnetic resonance imaging system for obtaining images of a part of the patient at a series of times through the surgical procedure for analysis by the surgical team to allow the surgical team to monitor the progress of the surgery, the magnetic resonance imaging system comprising:
 a magnet system comprising a cylindrical magnet of magnet wire defining a cylindrical bore within which a part of the patient is located for placement within high magnetic fields generated by the magnet;
 a control system for controlling and varying the magnetic fields;
 a radio frequency transmission and detection system for eliciting and detecting from the part of the patient nuclear magnetic resonance signals, in response to the magnetic field, including an RF probe arranged to be located adjacent to the part of the patient;
 and a computer and display monitor for decoding and displaying the detected signals;
 a support system supported from the floor mounting the magnet for movement relative to the table in a direction longitudinally of the table from a first imaging position at the table to a second non-imaging position;

wherein there is provided a location device for simulating a location of a bore of the magnet when moved to the table, the location device comprising:

a movable cart which can be moved into position at the magnet;

the movable cart carrying a first guide ring which simulates a location of a rear end of the bore of the magnet when the magnet is in the first imaging position;

a second guide ring arranged to be mounted on the table for engaging a front end of the bore of the magnet when the magnet is in the first imaging position;

and an elongate bar member spanning the first and second guide rings so that rotation of the elongate bar member around the first and second rings forms an imaginary cylindrical surface which matches the actual cylindrical surface of the bore when the magnet is in the first imaging position so that impingement of the bar member on any part of the patient or patient support predicts an unacceptable impingement of the magnet.

21. The apparatus according to claim 20 wherein the movable cart includes a locating coupling which engages the table to locate the cart at a predetermined location relative to the table and supports the first ring so that, when at the predetermined location, the first ring is located at a position simulating the rear end of the magnet.

22. The apparatus according to claim 20 wherein the second ring is mounted on a shielding assembly which is attached to the table.

23. The apparatus according to claim 22 wherein shielding assembly is removable from the table and is mounted on the movable cart for transport.

* * * * *